US010538570B2

(12) United States Patent
Leonard et al.

(10) Patent No.: US 10,538,570 B2
(45) Date of Patent: Jan. 21, 2020

(54) TARGETED AND MODULAR EXOSOME LOADING SYSTEM

(71) Applicant: Northwestern University, Evanston, IL (US)

(72) Inventors: Joshua N. Leonard, Wilmette, IL (US); Michelle E. Hung, Chicago, IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 14/502,494

(22) Filed: Sep. 30, 2014

(65) Prior Publication Data

US 2015/0093433 A1 Apr. 2, 2015

Related U.S. Application Data

(60) Provisional application No. 61/884,633, filed on Sep. 30, 2013.

(51) Int. Cl.

| | |
|---|---|
| ***C07K 14/705*** | (2006.01) |
| ***A61K 31/713*** | (2006.01) |
| ***C12N 15/88*** | (2006.01) |
| ***C12N 15/85*** | (2006.01) |

(52) U.S. Cl.

CPC .......... *C07K 14/705* (2013.01); *A61K 31/713* (2013.01); *C12N 15/85* (2013.01); *C12N 15/88* (2013.01); *C07K 2319/85* (2013.01)

(58) Field of Classification Search

CPC ............ A61K 31/713; A61K 47/48776; A61K 9/5068; C07K 14/705; C07K 2319/03; C07K 2319/06; C07K 2319/85; C12N 15/85; C12N 15/88; C12N 2795/00022

USPC ..... 424/450; 435/320.1, 375, 455; 514/44 A

See application file for complete search history.

(56) References Cited

U.S. PATENT DOCUMENTS

2007/0298118 A1* 12/2007 Lotvall .................. C12N 15/87 424/577

2013/0053426 A1* 2/2013 Seow ................. A61K 48/0025 514/44 A

OTHER PUBLICATIONS

Zhu et al. Am J Cardiovasc Dis 2011;1(2):138-149.*

Keryer-Bibens (2010; Biol. Cell (2008) 100, 125-138 (Printed in Great Britain)).*

Raposo et al. (J. Cell Biol. vol. 200, No. 4, pp. 373-383).*

Raposo et al. (J. Cell Biol. vol. 200, No. 4, pp. 373-383). (Year: 2013).*

Akao, Y., et al., Microvesicle-mediated RNA molecule delivery system using monocytes/macrophages. Mol Ther, 2011. 19(2): p. 395-9.

Alvarez-Erviti, L., et al., Delivery of siRNA to the mouse brain by systemic injection of targeted exosomes. Nat Biotechnol, 2011. 29(4): p. 341-5.

Iguchi, H., N. Kosaka, and T. Ochiya, Secretory microRNAs as a versatile communication too. Commun Integr Biol, 2010. 3(5): p. 478-81.

Johnstone, R.M., et al., Vesicle formation during reticulocyte maturation. Association of plasma membrane activities with released vesicles (exosomes). J Biol Chem, 1987. 262(19): p. 9412-20.

Keryer-Bibens, C., C. Barreau, and H.B. Osborne, Tethering of proteins to RNAs by bacteriophage proteins. Biol Cell, 2008. 100(2): p. 125-38.

Kosaka, N., et al., Competitive interactions of cancer cells and normal cells via secretory microRNAs. J Biol Chem, 2012. 287(2): p. 1397-405.

Kucharzewska, P., et al., Exosomes reflect the hypoxic status of glioma cells and mediate hypoxia-dependent activation of vascular cells during tumor development. Proc Natl Acad Sci U S A, 2013. 110(18): p. 7312-7.

Mizrak, A., et al., Genetically engineered microvesicles carrying suicide mRNA/protein inhibit schwannoma tumor growth. Mol Ther, 2013. 21(1): p. 101-8.

Montecalvo, A., et al., Mechanism of transfer of functional microRNAs between mouse dendritic cells via exosomes. Blood, 2012. 119(3): p. 756-66.

Ohno, S., et al., Systemically injected exosomes targeted to EGFR deliver antitumor microRNA to breast cancer cells. Mol Ther, 2013. 21(1): p. 185-91.

Raposo, G., et al., B lymphocytes secrete antigen-presenting vesicles. J Exp Med, 1996. 183(3): p. 1161-72.

Rechavi, O., et al., Cell contact-dependent acquisition of cellular and viral nonautonomously encoded small RNAs. Genes Dev, 2009. 23(16): p. 1971-9.

Skokos, D., et al., Mast cell-dependent B and T lymphocyte activation is mediated by the secretion of immunologically active exosomes. J Immunol, 2001. 166(2): p. 868-76.

Bolukbasi, M.F., et al., miR-1289 and "Zipcode"-like Sequence Enrich mRNAs in Microvesicles. Mol Ther Nucleic Acids, 2012. 1: p. e10.

Hergenreider, E., et al., Atheroprotective communication between endothelial cells and smooth muscle cells through miRNAs. Nat Cell Biol, 2012. 14(3): p. 249-56.

Koppers-Lallic, D.H., M.; van Eijndhoven, M.E.; Sabogal Pineros, Y.; Sie, D.; Ylstra, B.; Middeldorp, J.M.; Pegtel, D.M., Comprehensive deep-sequencing analysis reveals non-random small RNA incorporation into tumour exosomes and biomarker potential. Journal of Extracellular Vesicles, 2013. 2: p. 20826.

Lotvall, J.O.V., H., Exosome transfer of nucleic acids to cells, USPTO, 2007.

(Continued)

*Primary Examiner* — Janet L Epps-Smith

(74) *Attorney, Agent, or Firm* — Foley & Lardner LLP

(57) ABSTRACT

Disclosed are exosomes that include a packaging protein and a cargo RNA in which the packaging protein binds specifically to the cargo RNA. The packaging protein is a fusion protein that includes an RNA-binding domain and an exosome-targeting domain. The cargo RNA includes an RNA-motif that the RNA-binding domain of the fusion protein binds specifically such that the cargo RNA is packaged in the lumen of the exosomes.

11 Claims, 6 Drawing Sheets

Specification includes a Sequence Listing.

(56) References Cited

OTHER PUBLICATIONS

Valadi, H., et al., Exosome-mediated transfer of mRNAs and microRNAs is a novel mechanism of genetic exchange between cells. Nat Cell Biol, 2007. 9(6): p. 654-9.
Zitvogel, L., et al., Eradication of established murine tumors using a novel cell-free vaccine: dendritic cell-derived exosomes. Nat Med, 1998. 4(5): p. 594-600.
Hung, et al., "A Platform for Actively Loading Cargo RNA to Elucidate Limiting Steps in EV-Mediated Delivery", Journal of Extracellular Vesicles, 2016, 5: 31027, pp. 1-13.

* cited by examiner

1. Exosome Production

Plasma Membrane Proteins

Fig. 3

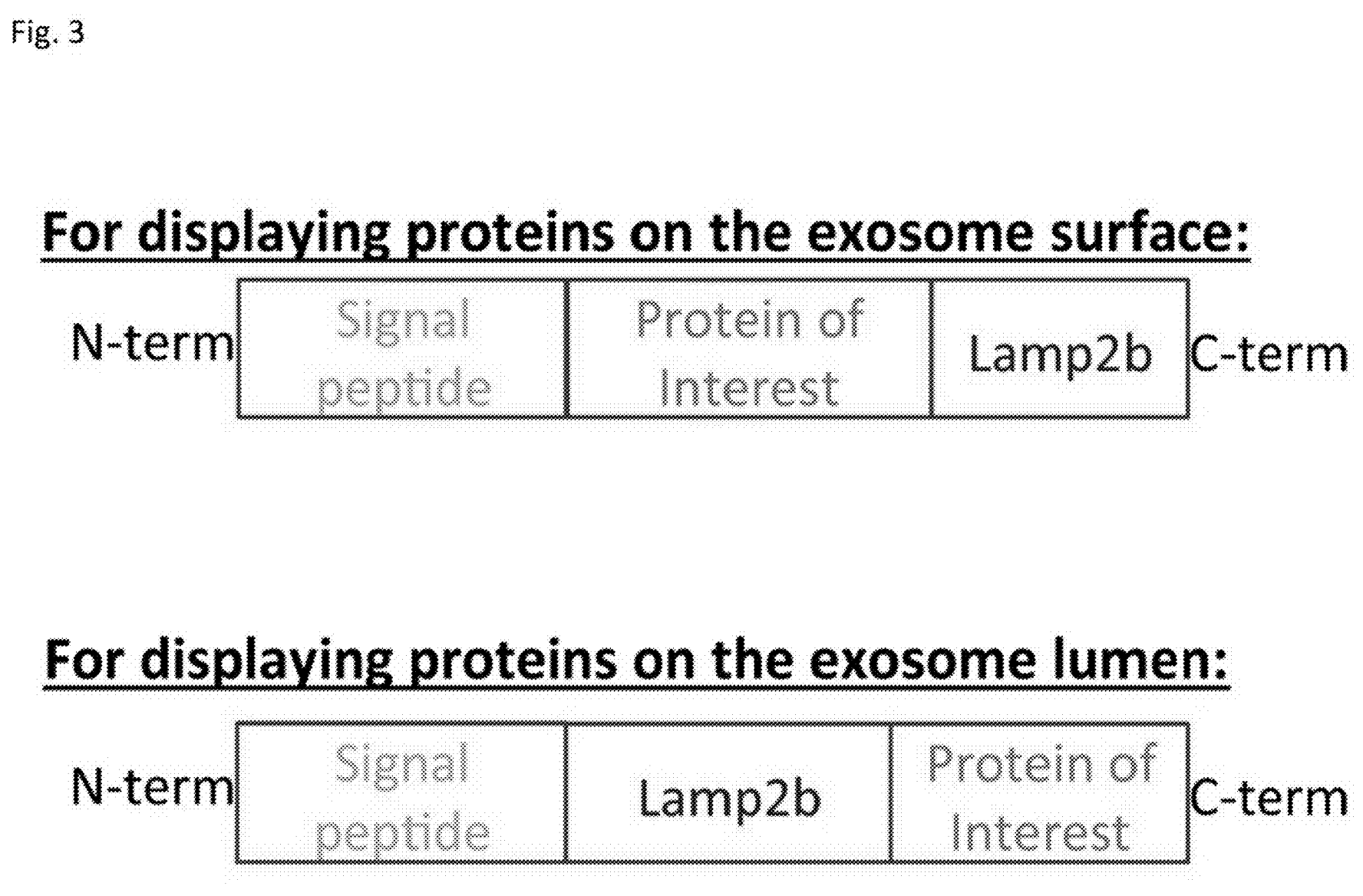

For displaying proteins on the exosome surface:

N-term | Signal peptide | Protein of Interest | Lamp2b | C-term

For displaying proteins on the exosome lumen:

N-term | Signal peptide | Lamp2b | Protein of Interest | C-term

N-term
Signal peptide
Lamp2b
MS2 Coat Protein
C-term
MS2 loop(s)
5'
Cargo sequence
$A_n$
5'-fusion
5'
Cargo sequence
$A_n$
3'-fusion cargo RNA only + negative control protein
cargo RNA +TAMEL packaging protein
Long cargo RNA - Cells
Cargo RNA/GAPDH
2.0E-02
1.5E-02
1.0E-02
5.0E-03
0.0E+00
*
*
no Loop
HA MS2 Loop
Long cargo RNA- Exosomes
Cargo RNA/GAPDH
10.0
8.0
6.0
4.0
2.0
0.0
*
no Loop
HA MS2 Loop

TARGETED AND MODULAR EXOSOME LOADING SYSTEM

CROSS-REFERENCE TO RELATED PATENT APPLICATIONS

The present application claims the benefit of priority under 35 U.S.C. § 119(e) to U.S. Provisional Patent Application No. 61/884,633, filed on Sep. 30, 2013, the content of which is incorporate herein by reference in its entirety.

STATEMENT REGARDING FEDERALLY SPONSORED RESEARCH OR DEVELOPMENT

This invention was made with government support under grant number P50 CA090386 awarded by the National Institutes of Health, and DGE0824162 awarded by the National Science Foundation. The government has certain rights in the invention.

BACKGROUND

The field of the invention relates to the use of lipid particles for delivering biological molecules to target cells. In particular, the field of the invention relates to engineered exosomes that contain and are used to target and deliver cargo RNA molecules to a target cell.

Exosomes are nanometer-scale lipid vesicles that are produced by many cell types and transfer proteins, nucleic acids, and other molecules between cells in the human body, as well as those of other animals. RNA-loaded exosomes have a wide variety of potential therapeutic uses and are already being investigated as delivery vehicles for gene therapy, vaccines, and reprogramming factors in the generation of pluripotent stem cells. However, the therapeutic utility of exosomes is hampered by a general lack of control over which molecules are loaded from the exosome-producer cell into the exosomes. Of particular relevance, efficiently loading of certain RNA species into exosomes is not possible using current technologies. The Targeted And Modular Exosome Loading (TAMEL) system described here is a technology for loading specific target RNAs into exosomes, in a manner that is independent of natural mechanisms for exosome loading. Thus, this technology enables control over which RNA species are most abundant in exosomes and may enable loading of various therapeutically-relevant RNA species.

SUMMARY

Disclosed are exosomes comprising a packaging protein and a cargo RNA in which the packaging protein binds specifically to the cargo RNA. The packaging protein is a fusion protein that includes an RNA-binding domain and an exosome-targeting domain. The cargo RNA includes an RNA-motif that the RNA-binding domain of the fusion protein binds specifically such that the cargo RNA is packaged in the lumen of the exosomes via the packaging protein.

Suitable RNA-binding domains for the fusion protein may include RNA-binding domains of bacteriophage proteins. In some embodiments, the RNA-binding domain of the fusion protein is the RNA-binding domain of the coat protein of the MS2 bacteriophage or R17 bacteriophage. In other embodiments, the RNA-binding domain of the fusion protein is the RNA-binding domain of N-protein of a lambdoid bacteriophage, such as N-protein of lambda bacteriophage, N-protein of P22 bacteriophage, or N-protein of phi21 bacteriophage. Accordingly, suitable RNA-motifs for the cargo RNA may include the corresponding high affinity binding loop of RNA of MS2 bacteriophage to which the MS2 coat protein binds, or the corresponding high affinity binding loop of RNA of the lambdoid bacteriophage to which the N-protein binds.

Suitable exosome-targeting domains may include exosome-targeting domains of lysosome-associated proteins. In some embodiments, the exosome-targeting domain is present in a lysosome membrane protein which may include, but is not limited to, a lysosome-associated membrane protein (LAMP) having a luminal N-terminus and a cytoplasmic C-terminus (e.g., LAMPs) and a lysosome integrated membrane protein (LIMPs). In some embodiments, the fusion protein may comprise the RNA-binding domain of a bacteriophage protein fused to the C-terminus of the lysosome membrane protein. Optionally, a ligand that targets the exosomes to target cells may be present at the N-terminus of the fusion protein and expressed or present on the surface of the exosome where the ligand binds specifically to a receptor on the surface of the target cells.

Suitable cargo RNA may include a hybrid RNA composing the RNA-motif fused at the 5'-terminus or 3'-terminus of miRNA, shRNA, mRNA, ncRNA, or any combination of these RNAs. The cargo RNA may be a therapeutic RNA for delivery to a target cell.

Also disclosed are methods for preparing the exosomes disclosed herein. The methods may include (a) expressing in a eukaryotic cell the fusion protein and (b) transducing in the eukaryotic cell the cargo RNA. In some embodiments, the exosomes are prepared by (a) transfecting the eukaryotic cell with a vector for expressing the fusion protein comprising the RNA-binding domain and the exosome-targeting domain, and (b) transducing into the eukaryotic cell the cargo RNA comprising an RNA-motif that binds to the RNA-binding domain of the fusion protein. In other embodiments, the methods may include expressing in a eukaryotic cell the fusion protein and expressing in the eukaryotic cell the cargo RNA. The fusion protein and cargo RNA may be expressed from a single vector (i.e., a single vector for expressing the fusion protein and the cargo RNA) or separate vectors for expressing the fusion protein and the cargo RNA. In some embodiments, the fusion protein is expressed from a eukaryotic expression vector that is transfected into a eukarvotic cell and the cargo RNA is expressed in vitro from a prokaryotic expression vector where the cargo RNA thus produced is subsequently transduced into the eukaryotic cell.

Kits composing such vectors also are contemplated herein. The vectors may be the same vector (i.e., a single vector for expressing the fusion protein and the cargo RNA) or separate vectors for expressing the fusion protein and the cargo RNA. The kits may include additional components for preparing the exosomes disclosed herein.

Also disclosed are methods for delivering a cargo RNA to a target cell. The methods may include contacting the target cell with the exosomes disclosed herein. The targeted exosomes may comprise a fusion protein which comprises a ligand at the N-terminus of the fusion protein that targets the exosomes to target cells. As such, the ligand may be present on the surface of the exosome where the ligand binds specifically to a receptor on the surface of the target cells. The cargo RNA may include a therapeutic RNA for treating a disease or disorder when the cargo RNA is delivered to the target cells (e.g., a hybrid RNA comprising a miRNA, shRNA, mRNA, ncRNA, or any combination of any of these RNAs fused to the RNA-motif that binds to the RNA-biding domain of the fusion protein). The exosomes may be formulated as a pharmaceutical composition for treating the disease or disorder.

BRIEF DESCRIPTION OF THE DRAWINGS

FIG. 3. Schematic representation of one embodiment of fusion proteins as contemplated herein. (Top) LAMP2b fusion proteins for expressing a protein of interest on the exosome surface; (Bottom) LAMP2b fusion proteins for expressing a protein of interest on the exosome lumen.

DESCRIPTION

Figure 1:
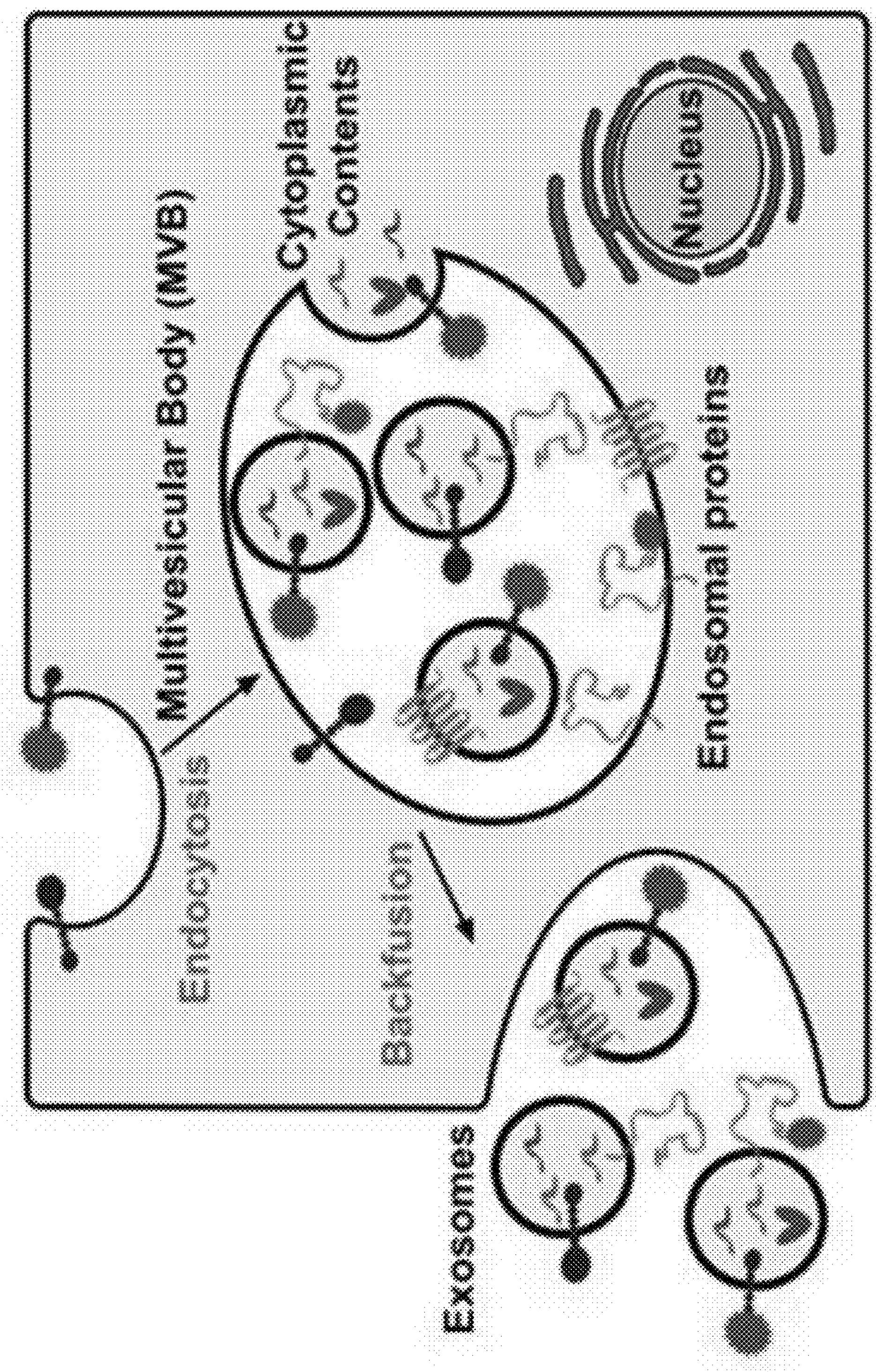
FIG. 1. Exosome Production: Exosomes are formed when the intraluminal vesicles of a multivesicular body (MVB) are released during MVB backfusion with the cell's outer membrane. Exosomes encapsulate endosomal membrane proteins, plasma membrane proteins, and cytoplasmic proteins and RNA.

The present invention is described herein using several definitions, as set forth below and throughout the application.

Unless otherwise specified or indicated by context, the terms "a", "an", and "the" mean "one or more." For example, "a protein" or "an RNA" should be interpreted to mean "one or more proteins" or "one or more RNAs," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

Disclosed herein are exosomes comprising a packaging protein and a cargo RNA in which the packaging protein binds specifically to the cargo RNA and targets the cargo RNA to the exosome. The disclosed exosomes may be characterized as packaging vehicles for the cargo RNA contained therein.

The disclosed exosomes utilize, as a packaging protein, a fusion protein comprising an RNA-binding domain and an exosome-targeting domain. The RNA-binding domain of the fusion protein binds an RNA-motif on the cargo RNA and the exosome-targeting domain of the fusion protein targets the fusion protein and bound cargo RNA to the exosome.

Suitable RNA-binding domains and RNA-motifs may include, but are not limited to, RNA-binding domains and RNA-motifs of bacteriophage. (See, e.g., Keryer-Bibens et al., "Tethering of proteins to RNAs by bacteriophage proteins," Biol. Cell (2008) 100, 125-138, the content of which is incorporated herein by reference in its entirety).

In some embodiments of the disclosed exosomes, the RNA-binding domain of the fusion protein is an RNA-binding domain of coat protein of MS2 bacteriophage or R17 bacteriophage, which may be considered to be interchangeable. (See, Keryer-Bibens et al.; and Stockley et al., "Probing sequence-specific RNA recognition by the bacteriophage MS2 coat protein," Nucl. Acids. Res., 1995, Vol. 23, No. 13, pages 2512-2518, the content of which is incorporated herein by reference in us entirety). The full-length amino acid sequence of the coat protein of MS2 bacteriophage is provided herein as SEQ ID NO: 1. The fusion proteins disclosed herein may include the full-length amino acid sequence of the coat protein of MS2 bacteriophage or a variant thereof as contemplated herein having a percentage of sequence identity in comparison to the amino acid sequence of the coat protein of MS2 bacteriophage, or a fragment thereof comprising a portion of the coat protein of MS2 bacteriophage (e.g., the RNA-binding domain of MS2 or SEQ ID NO:2, comprising the amino acid sequence (2-22) of the coat protein of MS2 bacteriophage).

In embodiments where the fusion protein comprises an RNA-binding domain of coat protein of MS2 bacteriophage, the cargo RNA typically comprises an RNA-motif of MS2 bacteriophage RNA which may form a high affinity binding loop that binds to the RNA-binding domain of the fusion protein. (See Peabody et al., "The RNA binding site of bacteriophage MS2 coat protein," The EMBO J., vol. 12, no.2, pp.595-600, 1993, Keryer-Bibens et al.; and Stockley et al., the contents of which are incorporated herein by reference in their entireties). The RNA-motif of MS2 bacteriophage and R17 bacteriophage has been characterized. (See id.). The RNA-motif has been determined to comprise minimally a 21-nt stem-loop structure where the identity of the nucleotides forming the stem do not appear to influence the affinity of the coat protein for the RNA-motif, but where the sequence of the loop contains a 4-nt sequence (AUUA (SEQ ID NO:3)), which does influence the affinity of the coat protein for the RNA-motif. Also important, is an unpaired adenosine two nucleotides upstream of the loop. In some embodiments of the disclosed exosomes, the RNA-motif is a high affinity binding loop comprising a sequence and structure selected from the group consisting of:

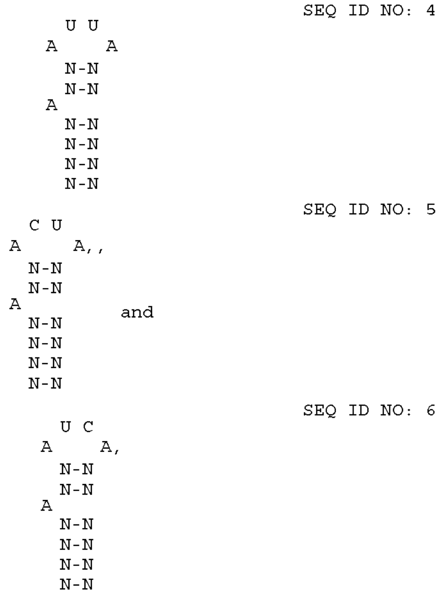

where N-N is any two base-paired RNA nucleotides (e.g., where each occurrence of N-N is independently selected from any of A-U, C-G, G-C, G-U, or U-G, and each occurrence of N-N may be the same or different). Specifically, the high affinity binding loop may comprise a sequence selected from the group consisting of SEQ ID NO:7 (5'-ACAUGAGGAUUACCCAUGU-3'), SEQ ID NO:8 (5'-ACAUGAGGAUUACCCAUGU-3"), and SEQ ID NO:9 (5'-ACAUGAGGAUCACCCAUGU-3'), or a variant thereof having a percentage sequence identity.

Preferably, the RNA-binding domain of the fusion protein binds to the RNA-motif with an affinity of at least about $1\times10^{-8}$ M. More preferably, the RNA-binding domain of the fusion protein binds to the RNA-motif with an affinity of at least about $1\times10^{-9}$ M, even more preferably with an affinity of at least about $1\times10^{-10}$ M.

In addition to the RNA-motif for binding to the RNA-binding domain of the fusion protein, the cargo RNA may include additional functional RNA sequences that be utilized for therapeutic purposes (e.g., miRNA, shRNA, mRNA, ncRNA, or a combination of any of these RNAs). (See Marcus et al., "FedExosomes: Engineering Therapeutic Biological Nanoparticles that Truly Deliver," Pharmaceuticals 2013, 6, 659-680, the content of which is incorporated herein by reference in its entirety). As such, the cargo RNA may be characterized as a hybrid RNA including the RNA-motif for binding to the RNA-binding domain of the fusion protein and including an additional RNA (e.g., miRNA, shRNA, mRNA, ncRNA, or a combination of any of these RNAs fused at the 5'-terminus or 3-terminus), which may be a therapeutic RNA.

In other embodiments of the disclosed exosomes, the RNA-binding domain of the fusion protein is an RNA-binding domain of the N-protein of a lambdoid bacteriophage, which may include but is not limited to lambda bacteriophage. P22 bacteriophage, and phi21 bacteriophage. (See, e.g., Keryer-Bibens et al.; Bahadur et al., "Binding of the Bacteriophage P22 N-peptide to the boxB RNA-motif Studied by Molecule Dynamics Simulations," Biophysical J., Vol., 97, December 2009, 3139-3149; Cilley et al., "Structural mimicry in the phage phi21 N peptide-boxB RNA complex," RNA (2003), 9:663-376; the contents of which are incorporated herein by reference in their entireties). The full-length amino acid sequence of the N-protein of lambda bacteriophage, P22 bacteriophage, and phi21 bacteriophage are provided herein as SEQ ID NOs:10, 11, and 12, respectively. The fusion proteins disclosed herein may include the amino acid sequence of the N-protein of the lambdoid bacteriophage or a variant thereof as contemplated herein having a percentage of sequence identity in comparison to the amino acid sequence of the N-protein of the lambdoid bacteriophage, or a fragment thereof comprising a portion of the N-protein of the lambdoid bacteriophage (e.g., the RNA-binding domain of the N-protein of any of lambda bacteriophage, P22 bacteriophage, and phi21 bacteriophage, or SEQ ID NOs:13, 14, and 15, comprising portions of the N -proteins of lambda bacteriophage, P22 bacteriophage, and phi21 bacteriophage, respectively).

In embodiments where the fusion protein comprises an RNA-binding domain of coat protein of a lambdoid bacteriophage, the cargo RNA typically comprises an RNA-motif of lambda bacteriophage RNA which may form a high affinity binding loop called 'boxB' that binds to the RNA-binding domain of the fusion protein, (See Keryer-Bibens et al,). BoxB of lambdoid bacteriophage has been characterized. (See id.; Bahadur, et al,; and Cilley et al.). For lambda bacteriophage, boxB has been determined to comprise minimally a 15-nt stem-loop structure where the identity of the nucleotides forming the stem and loop influence the affinity of the coat protein for the RNA-motif. (See Keryer-Bibens et al.). In some embodiments of the disclosed exosomes, the RNA-motif is a high affinity binding loop comprising a sequence and structure selected from the group consisting of:

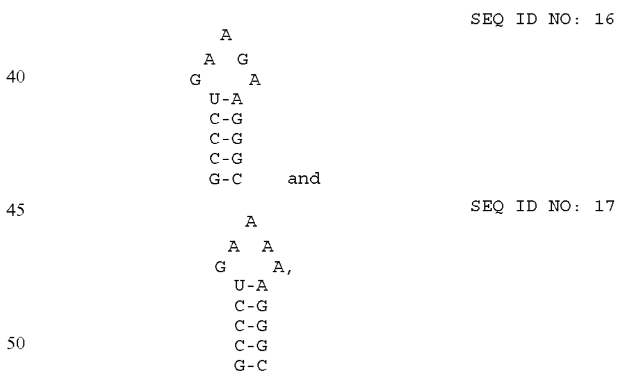

or a variant thereof having a percentage sequence identity, where the variant binds to the RNA-binding domain of the fusion protein. Preferably, the RNA-motif binds to the RNA-binding domain of the fusion protein with an affinity of at least about $1\times10^{-8}$ M, more preferably with an affinity of at least about $1\times10^{-9}$ M, even more preferably with an affinity of at least about $1\times10^{-10}$ M.

For P22 bacteriophage, boxB has been determined to comprise minimally a 15-nt stem-loop structure where the identity of the nucleotides forming the stem and loop influence the affinity of the coat protein for the RNA-motif, (See Bahadur et al.). In some embodiments of the disclosed exosomes, the RNA-motif is as high affinity binding, loop comprising a sequence and structure of:

SEQ ID NO: 18

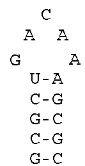

For phi21 bacteriophage. boxB has been determined to comprise minimally a 20-nt stem-loop structure where the identity of the nucleotides forming the stem and loop influence the affinity of the coat protein for the RNA-motif. (See Lilley et al.). In some embodiments of the disclosed exosomes, the RNA-motif is a high affinity binding loop comprising a sequence and structure of:

SEQ ID NO: 19

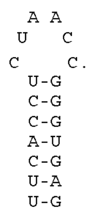

The fusion protein of the disclosed exosomes also includes an exosome-targeting domain. In some embodiments, the exosome-targeting domain is a domain of a lysosome-associated protein. Suitable lysosome-associated protein may include, but are not limited to, lysosome membrane proteins. (See Saftig, Lysosomes, Chapter 6, "Lysosome Membrane Proteins" 2004). Lysosome-associated membrane proteins (LAMPs) and lysosome integral membrane proteins (LIMPs) are the most abundant proteins of the lysosome membrane. (See id.).

In some embodiments, the exosome-targeting domain is an exosome-targeting domain of a LAMP. Suitable LAMPs may include, but are not limited to, LAMP-1 and LAMP-2, and isoforms thereof. (See Fukuda et al., "Cloning of cDNAs Encoding Human Lysosomal Membrane Glycoproteins, h-lamp-1 and h-lamp-2," J. Biol. Chem., Vol. 263, No. 35 December 1988, pp. 18920-18928: and Fukuda, "Lysosomal Membrane Glycoproteins," J. Biol. Chem., Vol. 266, No. 32, November 1991, pp. 21327, 21330.) LAMPs are lysosome-membrane proteins having a luminal (i.e., extra-cytoplasmic) N-terminus and a cytoplasmic C-terminus. (See id.). The mRNAs for expressing LAMPs may be processed differently to give isoforms. For example, there are three isoforms for LAMP-2 designated as LAMP-2a, LAMP-2b, and LAMP-2c. (See UniProt Database, entry number P13473—LAMP2_HUMAN, the contents of which is incorporated herein by reference in its entirety). LAMP-1 has a single isoform. (See UniProt Database, entry number P11279—LAMP1_HUMAN, the contents of which is incorporated herein by reference in its entirety). The full-length amino acid sequence of LAMP-2a, LAMP-2b, and LAMP-2c are provided herein as SEQ ID NOs:20, 21, and 22, respectively. The full-length amino acid sequence of LAMP-1 is provided herein as SEQ ID NO:26. The fusion proteins disclosed herein may include the full-length amino acid sequence of a LAMP or a variant thereof as contemplated herein having a percentage of sequence identity in comparison to the amino acid sequence of the wild-type LAMP, or a fragment thereof comprising a portion of the wild-type LAMP (e.g., SEQ ID NOs:23, 24, 25, and 27 comprising a portion of the C-termini of LAMP-2a, LAMP-2b, LAMP-2c, and LAMP-1, respectively).

For LAMPs, the C-terminus (e.g., comprising the 10-11 C-terminal amino acids) has been shown to be important for targeting LAMPS to lysosomes. (See id.; and Fukuda 1991). In some embodiments of the disclosed exosomes, the fusion protein comprises the RNA-binding domain fused to the C-terminus of one of SEQ ID NOs:23, 24, 25, and 27, which comprise a portion of the C-termini of LAMP-2a, LAMP-2b, LAMP-2c, and LAMP-1, respectively). The fusion protein may include the cytoplasmic domain of a LAMP and optionally may include additional amino acid sequences (e.g., at least a portion of the transmembrane domain and/or at least a portion of the luminal domain).

Optionally, the fusion protein of the disclosed exosomes further may comprise a ligand that targets the exosomes to target cells. The ligand may be present at the N-terminus of the fusion protein. For example, where the fusion protein comprises a portion of LAMP-2b and has a structure as follows: $N_{ter}$—signal peptide—ligand for target cell—transmembrane and cytosolic portion of LAMP-2b—RNA-binding domain-$C_{ter}$. (See Alvarez-Erviti et al.).

In some embodiments, the exosome-targeting domain is an exosome-targeting domain of a LIMP. Suitable LIMPs may include, but are not limited to, LIMP-1 (CD63) and LAMP-2, and isoforms thereof. LIMPs are lysosome-membrane proteins having one or more luminal domains, multiple transmembrane domains, and a cytoplasmic C-terminus. (See Ogata et al., "Lysosomal Targeting of Limp II Membrane Glycoprotein Requires a Novel Leu-Ile Motif at a Particular Position in Its Cytoplasmic Tail," J. Biol. Chem., Vol. 269, No. 7, February 1994, pp. 5210-5217). The mRNAs for expressing LIMPs may be processed differently to give isoforms. For example, there are three isoforms for LIMP-1 designated as LIMP-2a, LIMP-2b, and LIMP-2c and two isoforms for LIMP-2 designated as LIMP-2a and LIMP-2b. (See UniProt Database, entry number Q10148—SCRB2_HUMAN, and UniProt Database, entry number P08962—CD63_HUMAN, the contents of which is incorporated herein by reference in its entirety). The full-length amino acid sequence of LIMP-1a, LIMP-1b, and LIMP-1c are provided herein as SEQ ID NOs:28, 29, and 30, respectively. The full-length amino acid sequence of LIMP-2A and LIMP-2b are provided herein as SEQ ID NOs:32 and 33, respectively. The fusion proteins disclosed herein may include the full-length amino acid sequence of a LIMP or a variant thereof as contemplated herein having a percentage of sequence identity in comparison to the amino acid sequence of the wild-type LIMP, or a fragment thereof comprising a portion of the wild-type LIMP (e.g., SEQ ID NO:31 comprising a portion of the C-termini of LIMP-1a, LIMP-1b, LIMP-1C and SEQ ID NO:34 comprising a portion of the C-termini of LIMP-2a and LIMP-2b).

For LIMPs, the C-terminus (e.g., comprising the 14-19 C-terminal amino acids) has been shown to be important for targeting LAMPs to lysosomes. (See Ogata et al.). In some embodiments of the disclosed exosomes, the fusion protein comprises the RNA-binding domain fused to the C-terminus of one of SEQ ID NOs:31 and 34, which comprise a portion of the C-termini of LIMP-1a, LIMP-1b, LIMP -1c, and LIMP-2a and LIMP-2b). The fusion protein may include the cytoplasmic domain of a LIMP and optionally may include additional amino acid sequences (e.g., at least a portion of the transmembrane domain and/or at least a portion of the luminal domain).

The disclosed exosomes may be prepared by methods known in the art. For example, the disclosed exosomes may be prepare by expressing in a eukaryotic cell (a) an mRNA that encodes the fusion protein and (b) expressing in the eukaryotic cell the cargo RNA. The mRNA for the fusion protein and the cargo RNA may be expressed from vectors that are transfected into suitable production cells for producing the disclosed exosomes. The mRNA for the fusion protein and the cargo RNA may be expressed from the same vector (e.g., where the vector expresses the mRNA for the fusion protein and the cargo RNA from separate promoters), or the mRNA for the fusion protein and the cargo RNA may be expressed from separate vectors. The vector or vectors for expressing the mRNA for the fusion protein and the cargo RNA may be packaged in a kit designed for preparing the disclosed exosomes.

Also contemplated herein are methods for using the disclosed exosomes. For example, the disclosed exosomes may be used for delivering a cargo RNA to a target cell, where the methods include contacting the target cell with the disclosed exosomes. The disclosed exosomes may be formulated as part of a pharmaceutical composition for treating a disease or disorder and the pharmaceutical composition may be administered to a patient in need thereof to delivery the cargo RNA to target cells in order to treat the disease or disorder.

The disclosed exosomes may comprise novel proteins, polypeptides, or peptides. As used herein, the terms "protein" or "polypeptide" or "peptide" may be used interchangeable to refer to a polymer of amino acids. Typically, a "polypeptide" or "protein" is defined as a longer polymer of amino acids, of a length typically of greater than 50, 60, 70, 80, 90, or 100 amino acids. A "peptide" is defined as a short polymer of amino acids, of a length typically of 50, 40, 30, 20 or less amino acids.

A "protein" as contemplated herein typically comprises a polymer of naturally occurring ammo acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). The proteins contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myrtstoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine threonine or histidine).

The proteins disclosed herein may include "wild type" proteins and variants, mutants, and derivatives thereof. As used herein the term "wild type" is a term of the art understood by skilled persons and means the typical form of an organism, strain, gene or characteristic as it occurs in nature as distinguished from mutant or variant forms. As used herein, a "variant, "mutant," or "derivative" refers to a protein molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a mutant or variant molecule may one or more insertions, deletions, or substitution of at least one amino acid residue relative to a reference polypeptide (e.g., any of SEQ ID NOs: 1, 2, 10, 11, 12, 13, 14, 15, 20, 21, 22, 23. 24, and 25). The sequence of the full-length coat protein of MS2 bacteriophage, the sequence of the full-length N-protein of lambda bacteriophage, the sequence of the full-length N-protein of P22 bacteriophage, the sequence of the full-length N-protein of phi21 bacteriophage, the sequence of the full-length LAMP-2a, the sequence of the full-length LAMP-2b, and the sequence of the full-length LAMP-2c, are presented as SEQ ID NOs:1, 10, 11, 12, 20, 21, and 22, respectively, and may be used as a reference in this regard.

Regarding proteins, a "deletion" refers to a change in the amino acid sequence that results in the absence of one or more amino acid residues. A deletion may remove at least 1, 2, 3, 4, 5, 10, 20, 50, 100, 200, or more amino acids residues. A deletion may include an internal deletion and/or a terminal deletion an N-terminal truncation, a C-terminal truncation or both of a reference polypeptide).

Regarding proteins, "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full length polypeptide. For example, a fragment of a protein may comprise or consist essentially of a contiguous portion of an amino acid sequence of the full-length proteins of any of SEQ ID NOS: 1, 2, 10, 11, 12, 13, 14, 15, 20, 21, 22, 23, 24, and 25. A fragment may include an N-terminal truncation, a C-terminal truncation, or both truncations relative to the full-length protein.

Regarding proteins, the words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A variant of a protein may have N-terminal insertions, C-terminal insertions, internal insertions, or any combination of N-terminal insertions, C-terminal insertions, and internal insertions.

Regarding proteins, the phrases "percent identity" and "% identity," refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See. e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases. As described herein, variants, mutants, or fragments (e.g., a protein variant, mutant, or fragment thereof) may have 99%, 98%. 97%, 96%, 95%, 94%, 93%, 92%, 91%, 90%, 80%, 70%, 60%, or 50% amino acid sequence identity relative to a reference molecule (e.g., relative to any of SEQ ID NOs: 1, 2, 10, 11, 12, 13, 14, 15, 20, 23, 24, and 25).

Regarding proteins, percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Regarding proteins, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Gln, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed proteins, mutants, variants, or described herein may have one or more functional or biological activities exhibited by a reference polypeptide (e.g., one or more functional or biological activities exhibited by wild-type protein). For example, the disclosed proteins, mutants, variants, or derivatives thereof may have one or more biological activities that include binding to a single-stranded RNA, binding to as double-stranded RNA, binding to a target polynucleotide sequence, and targeting a protein to a lysosome or exosome.

The disclosed proteins may be substantially isolated or purified. The term "substantially isolated or purified" refers to proteins that are removed from their natural environment, and are at least 60% free, preferably at least 75% free, and more preferably at least 90% free, even more preferably at least 95% free from other components with which they are naturally associated.

Also disclosed herein are polynucleotides, for example polynucleotide sequences that encode proteins (e.g., DNA that encodes a polypeptide having the amino acid sequence of any of SEQ ID NOs:1, 2, 10, 11, 12, 13, 14, 15, 20, 21, 22, 23, 24, and 25 or a polypeptide variant having an amino acid sequence with at least about 50%, 60%, 70%, 80%, 90%, 95%, 96%, 97%, 98%, or 99% sequence identity to any of SEQ ID NOs: 1, 2, 10, 11, 12, 13, 14, 15, 20, 21, 22, 23, 24, and 25; DNA encoding, the polynucleotide sequence of any of SEQ ID NOs:3-9 and 16-19 or encoding a polynucleotide variant having a nucleotide sequence with at least about 50%, 60%, 70%, 80%, 90%, 95%, 96%, 97%, 98%, or 99% sequence identity to any of SEQ ID NOs:3-9 and 16-19; RNA comprising the polynucleotide sequence of any of SEQ ED NOs:3-9 and 16-19 or a polynucleotide variant having a nucleotide sequence with at least about 50%, 60%, 70%, 80%, 90%, 95%, 96%, 97%, 98%, or 99% sequence identity to any of SEQ ID NOs:3-9 and 16-19).

The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

Regarding polynucleotide sequences, the terms "percent identity" and "% identity" refer to the percentage of residue matches between at least two polynucleotide sequences aligned using a standardized algorithm. Such an algorithm may insert, in as standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized for expression in a particular host. In the art, codon usage frequency tables have been prepared for a number of host organisms including humans, mouse, rat, pig, *E. coli*, plants, and other host cells.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified," The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

"Transformation" or "transfected" describes a process by which exogenous nucleic acid (e.g., DNA or RNA) is introduced into a recipient cell. Transformation or transfection may occur under natural or artificial conditions according to various methods well known in the art, and may rely on any known method for the insertion of foreign nucleic acid sequences into a prokaryotic or eukaryotic host cell. The method for transformation or transfection is selected based on the type of host cell being transformed and may include, but is not limited to, bacteriophage or viral infection or non-viral delivery. Methods of non-viral delivery of nucleic acids include lipofection, nucleofection, microinjection, electroporation, heat shock, particle bombardment, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner. WO 91/17424 WO 91/16024. Delivery can be to cells (e.g. in vitro or ex vivo administration) or target tissues (e.g. in vivo administration). The term "transformed cells" or "transfected cells" includes stably transformed or transfected cells in which the inserted DNA is capable of replication either as an autonomously replicating plasmid or as part of the host chromosome, as well as transiently transformed or transfected cells which express the inserted DNA or RNA for limited periods of time.

The polynucleotide sequences contemplated herein may be present in expression vectors. For example, the vectors may comprise: (a) a polynucleotide encoding an ORF of a protein: (b) a polynucleotide that expresses an RNA that directs RNA-mediated binding, nicking, and/or cleaving of a target DNA sequence; and both (a) and (b). The polynucleotide present in the vector may be operably linked to a prokaryotic or eukaryotic promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter (e.g., a eukaryotic or prokaryotic promoter) operably linked to a polynucleotide that encodes a protein. A "heterologous promoter" refers to a promoter that is not the native or endogenous promoter for the protein or RNA that is being expressed. For example, a heterologous promoter for a LAMP may include a eukaryotic promoter or a prokaryotic promoter that is not the native, endogenous promoter for the LAMP As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The term "vector" refers to some means by which nucleic acid (e.g., DNA) can be introduced into a host organism or host tissue. There are various types of vectors including plasmid vector, bacteriophage vectors, cosmid vectors, bacterial vectors, and viral vectors. As used herein, a "vector" may refers to a recombinant nucleic acid that has been engineered to express a heterologous polypeptide (e.g., the fusion proteins disclosed herein). The recombinant nucleic acid typically includes cis-acting elements for expression of the heterologous polypeptide.

Any of the conventional vectors used for expression in eukaryotic cells may be used for directly introducing DNA into a subject. Expression vectors containing regulatory elements from eukaryotic viruses may be used in eukaryotic expression vectors (e.g., vectors containing SV40, CMV, or retroviral promoters or enhancers). Exemplary vectors include those that express proteins under the direction of such promoters as the SV40 early promoter. SV40 later promoter, metallothionein promoter, human cytomegalovirus promoter, murine mammary tumor virus promoter, and Rous sarcoma virus promoter. Expression vectors as contemplated herein may include eukaryotic or prokaryotic control sequences that modulate expression of a heterologous protein (e.g. the fusion protein disclosed herein). Prokaryotic expression control sequences may include constitutive or inducible promoters (e.g., T3, T7, Lac, up, or phoA), ribosome binding sites, or transcription terminators.

The vectors contemplated herein may be introduced and propagated in a prokaryote, which may be used to amplify copies of a vector to be introduced into a eukaryotic cell or as an intermediate vector in the production of a vector to be introduced into a eukaryotic cell (e.g. amplifying a plasmid as part of a viral vector packaging system). A prokaryote may be used to amplify copies of a vector and express one or more nucleic acids, such as to provide a source of one or more proteins for delivery to a host cell or host organism. Expression of proteins in prokaryotes may be performed using *Escherichia coli* with vectors containing constitutive or inducible promoters directing the expression of either a protein or a fusion protein comprising a protein or a fragment thereof. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; (iii) to aid in the purification of the recombinant protein by acting as a ligand in affinity purification (e.g., a His tag); (iv) to tag the recombinant protein for identification (e.g., such as Green fluorescence protein (GFP) or an antigen (e.g., HA) that can be recognized by a labelled antibody); (v) to promote localization of the recombinant protein to a specific area of the cell (e.g., where the protein is fused (e.g., at its N-terminus or C-terminus) to a nuclear localization signal (NLS) which may include the NLS of SV40, nucleoplasmin, C-myc M9 domain of hnRNP A1, or a synthetic NLS). The importance of neutral and acidic amino acids in NLS have been studied. (See Makkerh et al. (1996) *Curr Biol* 6(8):1025-1027). Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

The presently disclosed methods may include delivering one or more polynucleotides, such as or one or more vectors as described herein, one or more transcripts thereof, and/or one or proteins transcribed therefrom, to a host cell. Further contemplated are host cells produced by such methods, and organisms (such as animals, plants, or fungi) comprising or produced from such cells. The disclosed exosomes may be prepared by introducing vectors that express mRNA encoding a fusion protein and a cargo RNA as disclosed herein. Conventional viral and non-viral based gene transfer methods can be used to introduce nucleic acids in mammalian cells or target tissues. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell.

In the methods contemplated herein, a host cell may be transiently or non-transiently transfected stably (i.e., stably transfected) with one or more vectors described herein. In some embodiments, a cell is transfected as it naturally occurs in a subject (i.e., in situ). In some embodiments, a cell that is transfected is taken from a subject (i.e., explanted). In some embodiments, the cell is derived from cells taken from a subject, such as a cell line. Suitable cells may include stem cells (e.g., embryonic stem cells and pluripotent stem cells). A cell transfected with one or more vectors described herein may be used to establish a new cell line comprising one or more vector-derived sequences. In the methods contemplated herein, a cell may be transiently transfected with the components of a system as described herein (such as by transient transfection of one or more vectors, or transfection with RNA), and modified through the activity of a complex, in order to establish a new cell line comprising cells containing the modification but lacking any other exogenous sequence.

EXAMPLES

The following Examples are illustrative and are not intended to limit the scope of the claimed subject matter.

A Targeted and Modular Exosome Loading System

Figure 2:
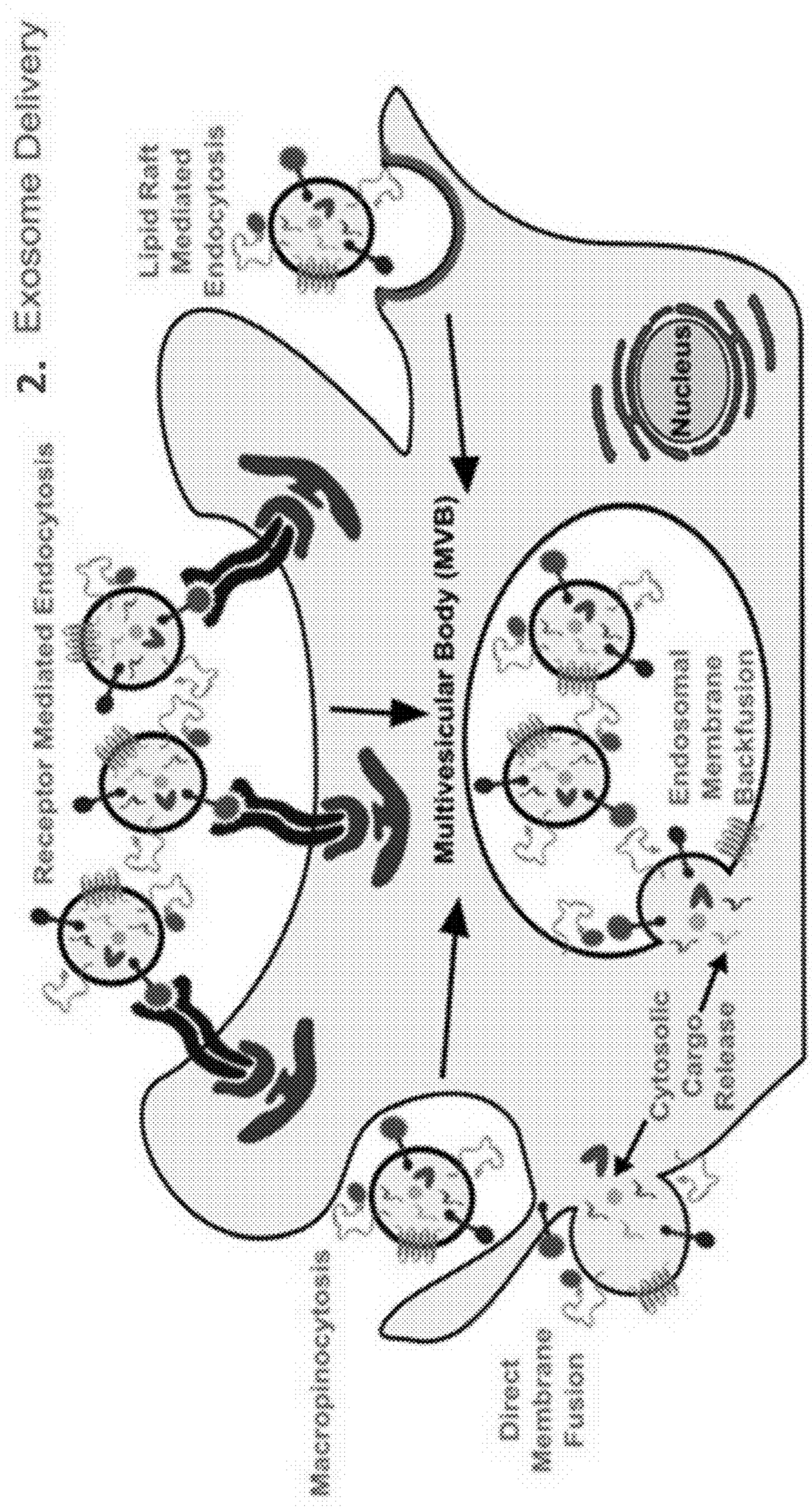
FIG. 2. Exosome Delivery: Exosomes are taken up by recipient cells by a variety of mechanisms, and exosome cargo is delivered to the cytoplasm of the recipient cell, where it is functional.

This Example relates to a Targeted and Modular Exosome Loading (TAMEL) system, which is as technology for directing the loading of RNA into exosomes. Secreted extracellular vesicles are emerging as important new features of the expanding landscape of intercellular communication. The process of secretion of exosomes by an exosome-producing cell and the process of uptake of the secreted exosomes by a recipient cell are illustrated schematically in FIGS. 1 and 2. A subset of extracellular vesicles in the 30-200 nanometer diameter range, known as exosomes, have been found to play a number of important roles in intercellular signaling, including shedding of obsolete proteins during reticulocyte maturation [1], presentation of antigens to T cells [2], activation of B and T cell proliferation [3], and induction of immune rejection of murine tumors, presumably by delivery or presentation of tumor antigens to the immune system [4]. Exosomes have generated great interest for their roles in intercellular communication and their potential to therapeutically modulate immune cell signaling. Subsequent investigations into exosome biogenesis, cargo packaging, and mediation of intercellular communication have identified new opportunities for harnessing and modifying exosomes to develop exosome-based therapeutics.

The TAMEL system disclosed here utilizes a "packaging protein" and a "cargo RNA." The packaging protein is an RNA-binding protein targeted to exosomes via fusion to an exosome-targeted domain of a lysosomal protein. The cargo RNA is an RNA molecule displaying the proper RNA-motif for binding by the packaging protein. This packaging system is novel in that it is the first method by which any type of RNA miRNA, shRNA, mRNA, ncRNA) can be targeted for loading into exosomes via fusion to the RNA-motif, without the need for overexpression of the RNA of interest. Overexpression generally is disfavored because it can alter the physiology of the exosome-producing cell. The ability to selectively enrich RNAs in exosomes is essential to the engineering of exosomes as therapeutic delivery vehicles. RNA-loaded exosomes have a wide variety of potential therapeutic uses and are already being investigated as delivery vehicles for gene therapy, vaccines, and reprogramming factors in the generation of pluripotent stem cells. However, the therapeutic utility of exosomes is hampered by a general lack of control over which molecules are loaded from the parent cell into the exosomes. The technology disclosed herein provides the capability to control which RNA species are most abundant in exosomes.

Description

In this example, the TAMEL packaging protein consists of an RNA-binding protein fused to Lamp2b. Lamp2b has been previously shown to localize to exosomes [5]. Alvarez-Erviti et al. determined the orientation of Lamp2b in exosomes (N-terminus on the exterior of exosomes, C-terminus on the interior of exosomes) and showed that peptides fused to the N-terminus of Lamp2b could be displayed on the outside of exosomes [5]. (See FIG. 3 for schematic examples of Lamp2b fusion proteins for expressing a protein of interest on the surface of an exosome versus the lumen of the exosome). To direct the loading of RNA into the lumen of the exosome, we fused an RNA-binding protein to the C-terminus of Lamp2b. (See FIG. 4). We have tested the system using RNA-binding proteins that have been previously characterized, including bacteriophage coat proteins from the MS2 and LambaN bacteriophages [6].

The TAMEL system of this Example may be implemented as follows: (a) an RNA-binding protein, such as a bacteriophage coat protein, is chosen; (b) a packaging protein comprising Lamp2b on the N-terminus and the RNA-binding protein on the C-terminus is designed (see FIG. 4); (c) cargo RNA containing the packaging protein binding motif is designed (see FIG. 4); (d) DNA sequences encoding the packaging protein and cargo RNA are generated (by molecular biology and/or DNA synthesis) and inserted into a suitable expression vector (e.g., viral vector for cargo RNA, plasmid or viral vector for packaging protein); (e) the cargo RNA expression vector is transduced into a suitable cell for producing RNA (or RNA is produced in vitro and transduced into a suitable cell for producing exosomes) and the packaging protein vector is transfected or transduced into a suitable cell line for producing exosomes; (f) exosomes are harvesting from the cell line producing the exosomes; and (g) RNA is isolated from these exosomes and quantified by qPCR.

The mode of action of the TAMEL system is that the packaging protein fused to Lamp2b is capable both of localizing to exosomes through its Lamp2b domain and binding RNA through its RNA-binding domain. During the process of exosome biogenesis, the RNA-binding domain is initially localized in the cytoplasm, where it has access to cytoplasmic RNA species, including the cargo RNA. The inward budding of the multivesicular body (MVB) membrane to form intraluminal vesicles (ILVs), results in the RNA-binding domain localizing in the lumen of ILVs. Bound RNA should move in concert with the RNA-binding domain, also localizing to the ILV lumen. As ILVs are released from the exosome-producing cell, as exosomes, the RNA-binding domain and bound RNA remain in the vesicle lumen, ultimately resulting in their presence in the lumen of exosomes. (See FIG. 1). After being released from an exosome-producing cell, the exosomes may be delivered to a target cell (i.e., recipient cell) where the exosomes are taken up and the exosome cargo is delivered to the cytoplasm of the target cell. (See FIG. 2).

Figure 5:
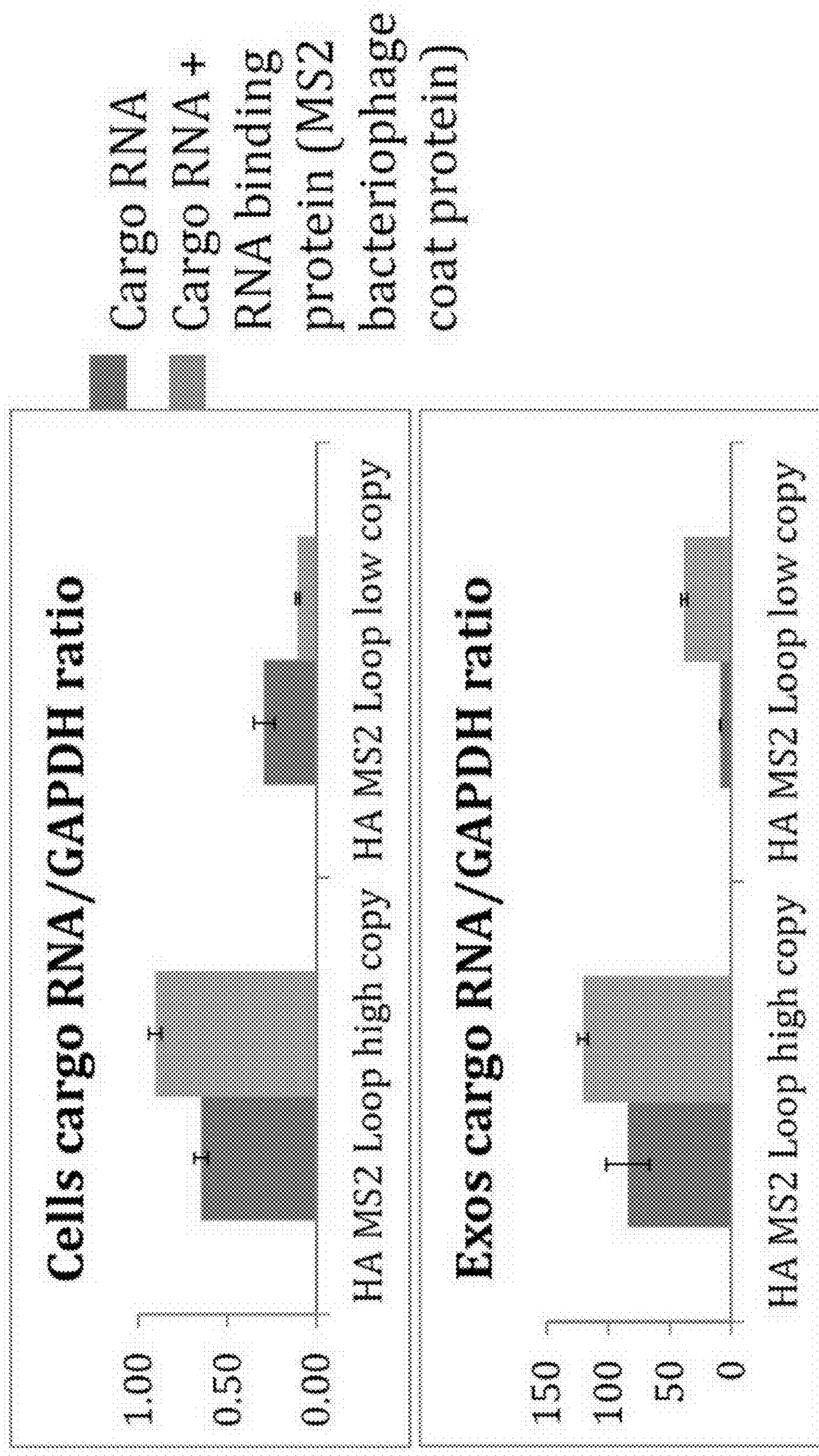
FIG. 5. Packaging of cargo RNA comprising the MS2 RNA packaging signal into exosomes in the presence of a fusion protein comprising the MS2 coat protein RNA-binding domain FIG. 6. Packaging of long cargo RNA into exosomes in the presence of TAMEL packaging protein.
Figure 6:
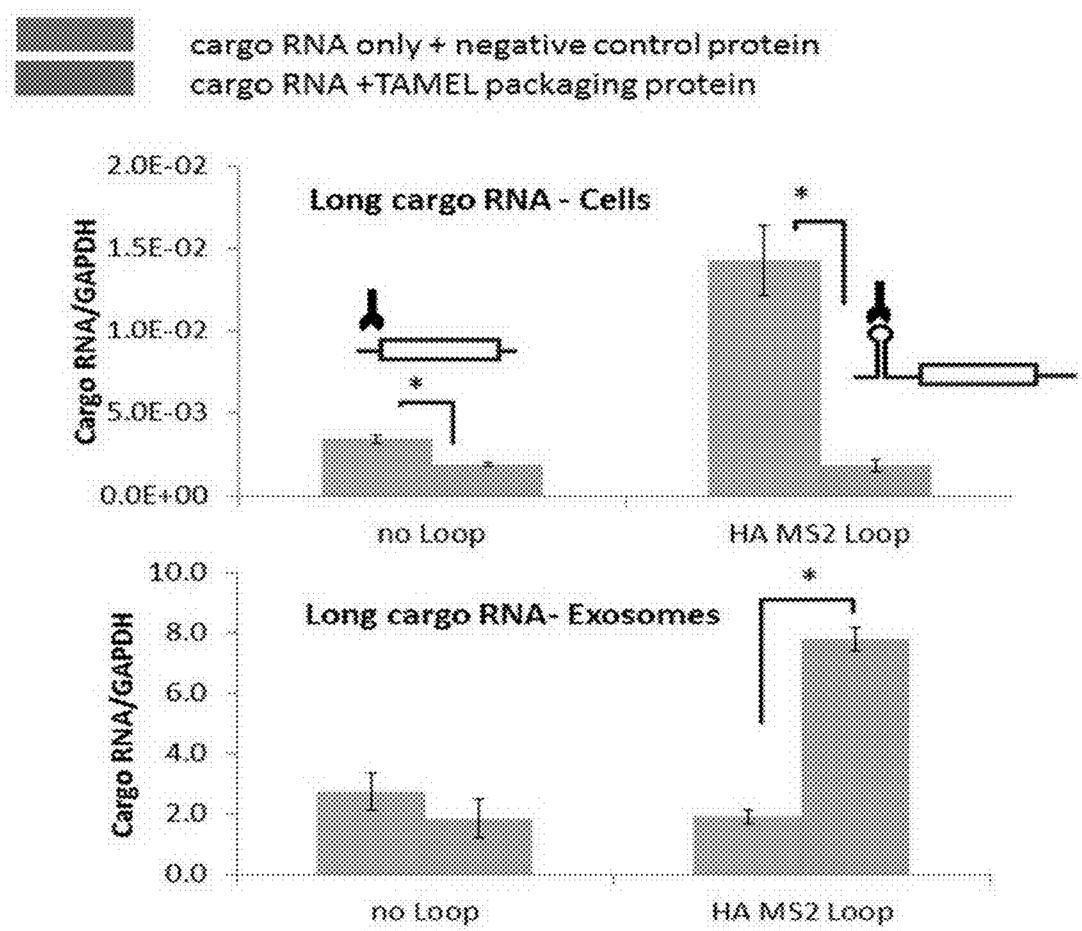

As illustrated in FIG. 5, cargo RNA bearing the MS2 RNA-binding loop was transduced into cells at high or low copy number, either in the presence or absence of the TAMEL packaging protein bearing the RNA-binding domain of the coat protein of MS2. The cargo RNA was a 187 base pair small RNA displaying the high affinity MS2 binding loop (HA MS2 Loop). The cargo RNA was transduced into cells at high copy or low copy number for high or low expression, respectively. Cargo RNA levels were normalized to GAPDH reference RNA in (top) cells and (bottom) exosomes. An observed increase in cargo RNA level in exosomes was significant by a student's t-test at a p-value of 0.05. Therefore, the TAMEL system increased the incorporation of a small (~190 bp) RNA into exosomes. In the presence of the Lamp2b-MS2 TAMEL packaging protein, the small cargo RNA level increased 1.4-4.4 fold in exosomes compared to no TAMEL packaging protein.

Figure 4:
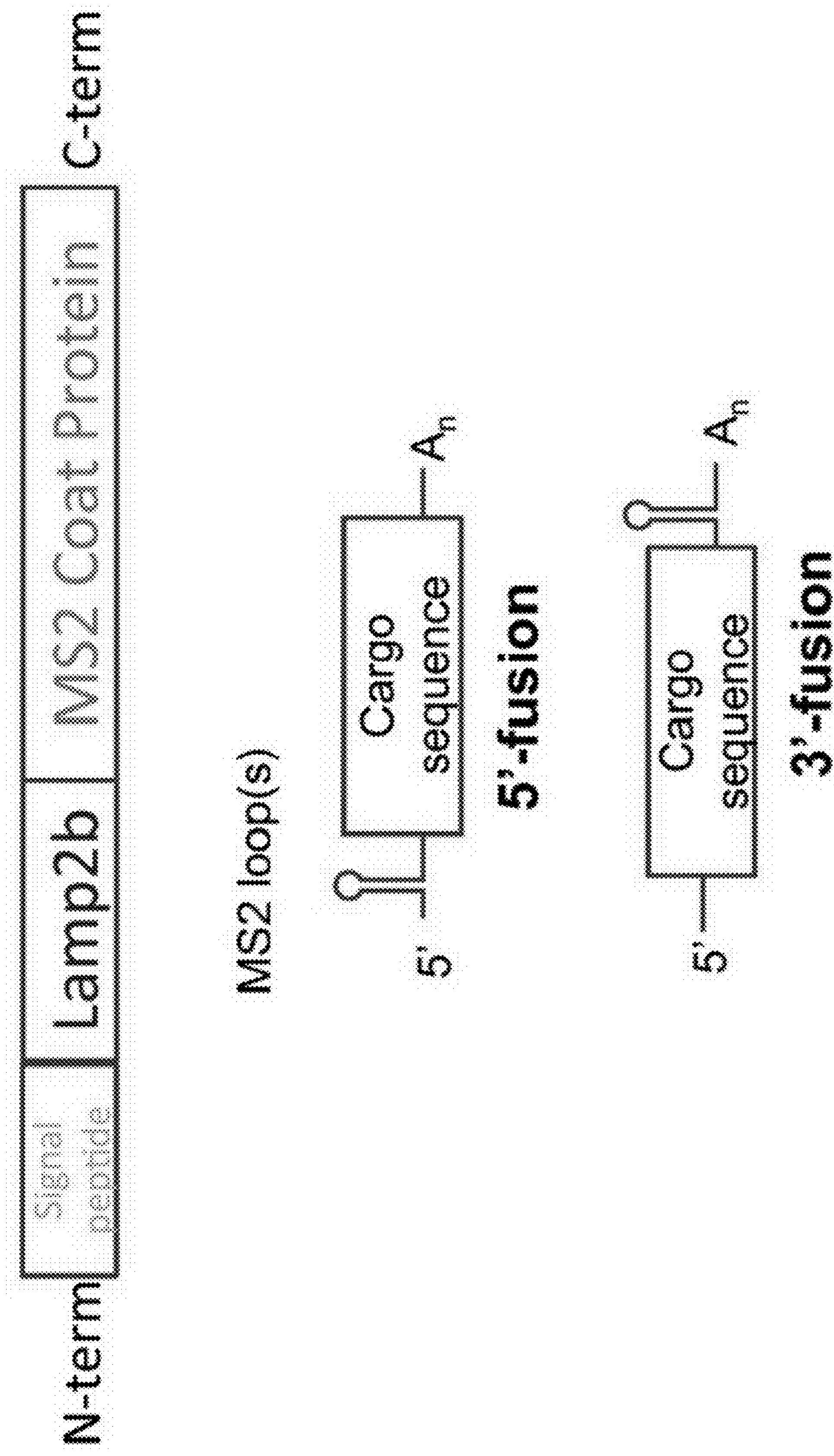
FIG. 4. Schematic representation of one embodiment of a packaging protein and cargo RNA as contemplated herein. The packaging protein is a fusion protein comprising from N-terminus to C-terminus: a signal peptide, at least a portion of LAMP2b comprising the exosome-targeting domain, and at least a portion of the MS2 coat protein comprising the RNA-binding domain. The cargo RNA comprises the high affinity binding loop of MS2 RNA fused at the 5'-terminus (top) or 3'-terminus (bottom) of a cargo sequence of interest.

To investigate whether "longer" cargo RNA could be incorporated into exosomes using the TAMEL system, we engineered lentiviral vectors driving expression of cargo RNA (~1700 nt plus 100-250 poly-A) via RNA Pol II. These cargo RNAs had either no MS2 binding loop or a high affinity MS2 binding loop, facilitating the cargo RNA to be bound by the Lamp2b-MS2 TAMEL packaging protein. We transfected cell lines with the Lamp2b-MS2 TAMEL packaging protein or a negative control protein (Lamp2b-neg). (See FIG. 4). Despite the fact that the cells transfected with the TAMEL packaging protein had lower levels of cargo RNA than those transfected with the negative control protein (FIG. 4, top), the presence of the TAMEL packaging protein increased the incorporation of the cargo RNA into exosomes by about 7 fold (FIG. 4, bottom versus top). These results indicate that the TAMEL system can be applied to package large RNAs into exosomes.

Discussion

The TAMEL system disclosed here offers advantages over two existing methods for enriching RNAs in exosomes: (1) overexpression and (2) RNA zipcodes [7]. Overexpression is a commonly utilized strategy for incorporating RNA into exosomes which comprises simply overexpressing the cargo RNA in the exosome-producing cells. This method potentially utilizes a mass action driving force to promote non-specific incorporation of cargo RNA into exosomes. Such cargo RNA overexpression in producer cells has been used to incorporate miRNA [8], [9], [10], chemically modified 3' benzen-pyridine miRNA [11], shRNA [9], and mRNA [12], [13] exosomes. Upon incubation of exosomes carrying these RNAs with recipient cells, these overexpressed RNAs were all functional (i.e. the mRNA was translated into protein, and the shRNAs and miRNAs induced target gene knockdown). This strategy thus appears to be broadly applicable to a variety of RNA cargos and recipient cell types.

Nonetheless, this technique has not been explored broadly enough to determine whether it is robust and widely applicable. The observation that some RNA species that are highly abundant in cells are not present in the exosomes produced from those cells [14], [15], [16], [17] suggests that this strategy may have varying degrees of success for different types of RNA, and indeed may be incapable of mediating the packaging of RNAs that may be actively excluded from exosomes. Furthermore, overexpression of RNA can impact host cell physiology, causing changes in cell health, or possibly changes in exosome production itself. These effects may hinder the packaging of certain RNAs into exosomes, for example therapeutic RNAs intended to induce apoptosis in cancer cells. In contrast, the described TAMEL system is not dependent on high expression levels of the cargo RNA. In fact, the platform could be engineered for greater sensitivity to RNAs that are expressed only at low levels (for example, by engineering higher affinity RNA-binding domains). Furthermore, because TAMEL is independent of host packaging mechanisms, it is capable of loading any RNA into exosomes, even RNAs that have been observed to be excluded from exosomes.

RNA zipcodes refer to structural and sequence motifs that have been identified as enriched in exosomes, and may be utilized to direct the loading of RNA into exosomes. For example, deep sequencing of exosome RNA revealed that miRNAs with 3' modifications are enriched in exosomes [18]. Potentially, 3' modification of miRNA could be used to load specific miRNAs into exosomes, but this has not been tested. In the case of mRNA, however, RNA zipcodes have been used to enrich mRNA in exosomes. RNA zipcodes are sequence motifs in the 3' untranslated region (UTR) that direct mRNA localization within the cell. Bolukbasi et al. identified two features—a miR-1289 binding site and a core "CTGCC" motif—that are enriched in the 3' UTRs of a large proportion of mRNAs found in glioblastoma- and melanoma-derived exosomes. Replacing the 3' UTR of eGFP with a 25 nucleotide sequence containing the miR-1289 binding site and the "CTGCC" motif added was sufficient to increase eGFP mRNA incorporation into HEK293T exosomes by 2-fold compared to untagged eGFP mRNA. Overexpression of miR-1289 further increased the incorporation of the construct 6-fold compared to the untagged eGFP mRNA. This increase in exosome targeting depended on the presence of the miR-1289 binding site, as mutation of this site abrogated enrichment of the mRNA in exosomes [7]. This approach to RNA loading applies only to mRNA, which contain a 3' UTR. Whether or not these zipcodes could be placed in non-coding and small RNAs to mediate loading into exosomes is unknown. Furthermore, overexpression of miR-1289 increases the levels of endogenous mRNAs containing miR-1289 binding sites loaded into exosomes [7] which could be undesirable for certain applications.

In contrast to these RNA-motifs, the TAMEL system can be applied to any type of RNA and does require interfering with native exosome loading mechanisms. As such, the TAMEL system is widely applicable. For example, the TAMEL system may be used: (a) to enrich exosomes with therapeutic RNA for use of exosomes as gene therapy delivery vehicles; (b) to enrich exosomes with RNA as part of an exosome vaccine; (c) to enrich exosomes with reprogramming RNAs for generating pluripotent stem cells; (d) to enrich exosomes with a specific RNA for delivering the RNA to recipient cells as an alternative to transfection or transduction; (e) to study and characterize the factors that affect loading of native RNA into exosomes via using the TAMEL system as a model and modifying various aspects of the TAMEL system to determine how the modifications affect RNA loading.

Notably, as demonstrated here, the present TAMEL system can be utilized to incorporate relatively long mRNAs. This result is important because this indicates that the TAMEL system will be useful for designing exosomes for delivering mRNAs to target cells, which could be useful in a variety of therapeutic applications.

REFERENCES

1. Johnstone, R. M., et al., Vesicle formation during reticulocyte maturation. Association of plasma membrane activities with released vesicles (exosomes). J Biol Chem, 1987. 262(19): p. 9412-20.

2. Raposo, G., et al., B lymphocytes secrete antigen-presenting vesicles. J Exp Med, 1996. 183(3): p. 1161-72.

3. Skokos, D., et al., Mast cell-dependent B and T lymphocyte activation is mediated by the secretion of immunologically active exosomes. J Immunol, 2001. 166(2): p. 868-76.

4. Zitvogel, L., et al., Eradication of established murine tumors using a novel cell-free vaccine: dendritic cell-derived exosomes. Nat Med, 1998. 4(5): p. 594-600.

5. Alvarez-Erviti, L., et al., Delivery of siRNA to the mouse brain by systemic injection of targeted exosomes. Nat Biotechnol, 2011. 29(4): p. 341-5.

6. Keryer-Bibens, C., C. Barreau, and H. B. Osborne, Tethering of proteins to RNAs by bacteriophage proteins. Biol Cell, 2008. 100(2): p. 125-38.

7. Bolukbasi, M. F., et al., miR-1289 and "Zipcode"-like Sequence Enrich mRNAs in Microvesicles, Mol Ther Nucleic Acids, 2012. 1: p. e10.

8. Ohno, S., et al., Systemically injected exosomes targeted to EGFR deliver antitumor microRNA to breast cancer cells. Mol Ther, 2013. 21(1): p. 185-91.

9. Rechavi, O., et al., Cell contact-dependent acquisition of cellular and viral nonautonomously encoded small RNAs. Genes Dev, 2009. 23(16): p. 1971-9.

10. Kosaka, N., et al., Competitive interactions of cancer cells and normal cells via secretory microRNAs. J Biol Chem, 2012, 287(2): p. 1397-405.

11. Akao, Y., et al., Microvesicle-mediated RNA molecule delivery system using monocytes/macrophages. Mol Ther, 2011, 19(2); p. 395-9.

12. Hergenreider, E., et al., Atheroprotective communication between endothelial cells and smooth muscle cells through miRNAs. Nat Cell Biol, 2012. 14(3): p. 249-56.

13. Mizrak, A., et al., Genetically engineered microvesicles carrying suicide mRNA/protein inhibit schwannoma tumor growth. Mol Ther, 2013. 21(1): p. 101-8.

14. Valadi, et al., Exosome-mediated transfer of mRNAs and microRNAs is a novel mechanism of genetic exchange between cells. Nat Cell Biol, 2007. 9(6): p. 654-9.

15. Montecalvo, A. et al., Mechanism of transfer of functional microRNAs between mouse dendritic cells via exosomes. Blood, 2012, 119(3); p. 756-66.

16. Iguchi, H., N. Kosaka, and T. Ochiya, Secretory microRNAs as a versatile communication tool. Commun Integr Biol, 2010. 3(5): p. 478-81.

17. Kucharzewska, P., et al., Exosomes reflect the hypoxic status of glioma cells and mediate hypoxia-dependent activation of vascular cells during tumor development. Proc Natl Acad Sci USA, 2013. 110(18): p. 7312-7.

18. Koppers-Lallic, D. H., M.; van Eijndhoven, M. E.; Sabogal Pineros, Y.; Sie, D.; Ylstra, B.; Middeldorp, J. M., Pegtel, D. M., Comprehensive deep-sequencing analysis reveals non-random small RNA incorporation into tumour exosomes and biomarker potential. Journal of Extracellular Vesicles, 2013.2: p. 20826.

19. Lotvall, J. O. V., H., Exosome transfer of nucleic acids to cells, USPTO, 2007.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. An exosome comprising a packaging protein and a cargo RNA that binds to the packaging protein, wherein the packaging protein is a fusion protein comprising an RNA-binding domain and an exosome-targeting domain that targets the fusion protein to the membrane of the exosome, wherein the exosome-targeting domain is a domain of a lysosome membrane protein having a luminal N-terminus and a cytoplasmic C-terminus, and wherein the cargo RNA comprises more than one binding loop and the RNA-binding domain of the fusion protein binds specifically to the binding loops of the cargo RNA, and further wherein the RNA-binding domain is the RNA-binding domain of MS2 bacteriophage coat protein comprising SEQ ID NO:2 or a variant thereof having at least 80% amino acid sequence identity to SEQ ID NO:2, and wherein the binding loops comprise a sequence and structure selected from the group consisting of:

SEQ ID NO: 4

```
  U U
A     A
  N-N
  N-N
A
  N-N
  N-N
  N-N
  N-N
```

-continued

SEQ ID NO: 5

```
  C U
A    A,,
  N-N
  N-N
A
  N-N      and
  N-N
  N-N
  N-N
```

SEQ ID NO: 6

```
   UC
 A    A,
  N-N
  N-N
 A
  N-N
  N-N
  N-N
  N-N
```

where N-N is any two base-paired RNA nucleotides.

2. The exosomes of claim 1, wherein the binding loops comprise a sequence selected from the group consisting of SEQ ID NO:7, SEQ ID NO:8, and SEQ ID NO:9, or a variant thereof having at least 80% nucleotide sequence identity to SEQ ID NO:7, SEQ ID NO:8, and SEQ ID NO:9, respectively.

3. The exosomes of claim 1, wherein the exosome-targeting domain comprises at its C-terminus a sequence selected from a group consisting of SEQ ID NO:23, SEQ ID NO:24, SEQ ID NO:25, SEQ ID NO:27, SEQ ID NO:31, and SEQ ID NO:34, or a variant thereof having at least 80% amino acid sequence identity to SEQ ID NO:23, SEQ ID NO:24, SEQ ID NO:25, SEQ ID NO:27, SEQ ID NO:31, and SEQ ID NO:34, respectively.

4. The exosomes of claim 3, wherein the exosome-targeting domain comprises at its C-terminus SEQ ID NO:24 or a variant thereof having at least 80% amino acid sequence identity to SEQ ID NO:24.

5. The exosomes of claim 4, wherein the RNA-binding domain is fused to the C-terminus of SEQ ID NO:24 or the variant thereof.

6. The exosomes of claim 1, wherein a ligand that targets the exosomes to target cells is present at the N-terminus of the fusion protein and is expressed on the surface of the exosomes.

7. The exosomes of claim 1, wherein the cargo RNA is a hybrid RNA comprising the binding loops and further comprising miRNA, shRNA, mRNA, ncRNA, or a combination of any of these RNAs.

8. A method for preparing the exosomes of claim 1, the method comprising (a) expressing in a eukaryotic cell an mRNA that encodes the fusion protein and (b) transducing into the eukaryotic cell the cargo RNA.

9. A method for delivering a cargo RNA to a target cell, the method comprising contacting the target cell with the exosomes of claim 1.

10. A kit comprising: (a) a vector for expressing a fusion protein comprising an RNA-binding domain and an exosome-targeting domain that targets the fusion protein to the membranes of exosomes, wherein the exosome-targeting domain is a domain of a lysosome membrane protein having a luminal N-terminus and a cytoplasmic C-terminus, and (b) a vector for expressing a cargo RNA comprising more than one binding loop that bind to the RNA-binding domain of the fusion protein, wherein the RNA-binding domain is the RNA-binding domain of MS2 bacteriophage coat protein comprising SEQ ID NO:2 or a variant thereof having at least 80% amino acid sequence identity to SEQ ID NO:2, and wherein the binding loops comprise a sequence and structure selected from the group consisting of:

SEQ ID NO: 4

```
 U U
A   A
 N-N
 N-N
A
 N-N
 N-N
 N-N
 N-N
```

SEQ ID NO: 5

```
 C U
A   A
 N-N
 N-N
A
 N-N
 N-N
 N-N
 N-N,
and
```

SEQ ID NO: 6

```
 U C
A   A
 N-N
 N-N
A
 N-N
 N-N
 N-N
 N-N,
```

where N-N is any two base-paired RNA nucleotides.

11. The kit of claim 10, wherein the vectors are separate vectors.

* * * * *

```
                          SEQUENCE LISTING


<160> NUMBER OF SEQ ID NOS: 34

<210> SEQ ID NO 1
<211> LENGTH: 130
<212> TYPE: PRT
<213> ORGANISM: Levivirus Bacteriophage MS2

<400> SEQUENCE: 1

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130


<210> SEQ ID NO 2
<211> LENGTH: 53
<212> TYPE: PRT
<213> ORGANISM: Levivirus Bacteriophage MS2

<400> SEQUENCE: 2

Tyr Lys Val Thr Cys Ser Val Arg Gln Ser Ser Ala Gln Asn Arg Lys
1               5                   10                  15

Tyr Thr Ile Lys Val Glu Val Pro Lys Val Ala Thr Gln Thr Val Gly
            20                  25                  30

Gly Val Glu Leu Pro Val Ala Ala Trp Arg Ser Tyr Leu Asn Met Glu
        35                  40                  45

Leu Thr Ile Pro Ile
    50


<210> SEQ ID NO 3
<211> LENGTH: 10
<212> TYPE: RNA
```

<213> ORGANISM: Levivirus Bacteriophage MS2
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: misc_feature
<222> LOCATION: (8)..(10)
<223> OTHER INFORMATION: n is a, c, g, or u

<400> SEQUENCE: 3 nnnauuannn 10

<210> SEQ ID NO 4
<211> LENGTH: 23
<212> TYPE: RNA
<213> ORGANISM: Levivirus Bacteriophage MS2
<220> FEATURE:
<221> NAME/KEY: misc_feature
<222> LOCATION: (1)..(7)
<223> OTHER INFORMATION: n is a, c, g, or u
<220> FEATURE:
<221> NAME/KEY: misc_feature
<222> LOCATION: (9)..(10)
<223> OTHER INFORMATION: n is a, c, g, or u
<220> FEATURE:
<221> NAME/KEY: misc_feature
<222> LOCATION: (15)..(23)
<223> OTHER INFORMATION: n is a, c, g, or u

<400> SEQUENCE: 4
nnnnnnnann auuannnnnn nnn 23

<210> SEQ ID NO 5
<211> LENGTH: 23
<212> TYPE: RNA
<213> ORGANISM: Levivirus Bacteriophage MS2
<220> FEATURE:
<221> NAME/KEY: misc_feature
<222> LOCATION: (1)..(7)
<223> OTHER INFORMATION: n is a, c, g, or u
<220> FEATURE:
<221> NAME/KEY: misc_feature
<222> LOCATION: (9)..(10)
<223> OTHER INFORMATION: n is a, c, g, or u
<220> FEATURE:
<221> NAME/KEY: misc_feature
<222> LOCATION: (15)..(23)
<223> OTHER INFORMATION: n is a, c, g, or u

<400> SEQUENCE: 5
nnnnnnnann aucannnnnn nnn 23

<210> SEQ ID NO 6
<211> LENGTH: 23
<212> TYPE: RNA
<213> ORGANISM: Levivirus Bacteriophage MS2
<220> FEATURE:
<221> NAME/KEY: misc_feature
<222> LOCATION: (1)..(7)
<223> OTHER INFORMATION: n is a, c, g, or u
<220> FEATURE:
<221> NAME/KEY: misc_feature
<222> LOCATION: (9)..(10)
<223> OTHER INFORMATION: n is a, c, g, or u
<220> FEATURE:
<221> NAME/KEY: misc_feature
<222> LOCATION: (15)..(23)
<223> OTHER INFORMATION: n is a, c, g, or u

<400> SEQUENCE: 6
nnnnnnnann acuannnnnn nnn 23

<210> SEQ ID NO 7
<211> LENGTH: 23
<212> TYPE: RNA
<213> ORGANISM: Levivirus Bacteriophage MS2

<400> SEQUENCE: 7
aaacaugagg auuacccaug ucg 23

<210> SEQ ID NO 8
<211> LENGTH: 23
<212> TYPE: RNA
<213> ORGANISM: Levivirus Bacteriophage MS2

<400> SEQUENCE: 8
aaacaugagg aucacccaug ucg 23

<210> SEQ ID NO 9
<211> LENGTH: 23
<212> TYPE: RNA
<213> ORGANISM: Levivirus Bacteriophage MS2

<400> SEQUENCE: 9
aaacaugagg acuacccaug ucg 23

<210> SEQ ID NO 10
<211> LENGTH: 107
<212> TYPE: PRT
<213> ORGANISM: Enterobacteria phage lambda

<400> SEQUENCE: 10

```
Met Asp Ala Gln Thr Arg Arg Arg Glu Arg Arg Ala Glu Lys Gln Ala
1               5                   10                  15

Gln Trp Lys Ala Ala Asn Pro Leu Leu Val Gly Val Ser Ala Lys Pro
            20                  25                  30

Val Asn Arg Pro Ile Leu Ser Leu Asn Arg Lys Pro Lys Ser Arg Val
        35                  40                  45

Glu Ser Ala Leu Asn Pro Ile Asp Leu Thr Val Leu Ala Glu Tyr His
    50                  55                  60

Lys Gln Ile Glu Ser Asn Leu Gln Arg Ile Glu Arg Lys Asn Gln Arg
65                  70                  75                  80

Thr Trp Tyr Ser Lys Pro Gly Glu Arg Gly Ile Thr Cys Ser Gly Arg
                85                  90                  95

Gln Lys Ile Lys Gly Lys Ser Ile Pro Leu Ile
            100                 105
```

<210> SEQ ID NO 11
<211> LENGTH: 100
<212> TYPE: PRT
<213> ORGANISM: Enterobacteria phage P22

<400> SEQUENCE: 11

```
Met Thr Val Ile Thr Tyr Gly Lys Ser Thr Phe Ala Gly Asn Ala Lys
1               5                   10                  15

Thr Arg Arg His Glu Arg Arg Arg Lys Leu Ala Ile Glu Arg Asp Thr
            20                  25                  30

Ile Cys Asn Ile Ile Asp Ser Ile Phe Gly Cys Asp Ala Pro Asp Ala
        35                  40                  45

Ser Gln Glu Val Lys Ala Lys Arg Ile Asp Arg Val Thr Lys Ala Ile
    50                  55                  60
```

```
Ser Leu Ala Gly Thr Arg Gln Lys Glu Val Glu Gly Gly Ser Val Leu
65                  70                  75                  80

Leu Pro Gly Val Ala Leu Tyr Ala Ala Gly His Arg Lys Ser Lys Gln
                85                  90                  95

Ile Thr Ala Arg
            100


<210> SEQ ID NO 12
<211> LENGTH: 99
<212> TYPE: PRT
<213> ORGANISM: Enterobacteria phage Phi21

<400> SEQUENCE: 12

Met Val Thr Ile Val Trp Lys Glu Ser Lys Gly Thr Ala Lys Ser Arg
1               5                   10                  15

Tyr Lys Ala Arg Arg Ala Glu Leu Ile Ala Glu Arg Arg Ser Asn Glu
            20                  25                  30

Ala Leu Ala Arg Lys Ile Ala Leu Lys Leu Ser Gly Cys Val Arg Ala
        35                  40                  45

Asp Lys Ala Ala Ser Leu Gly Ser Leu Arg Cys Lys Lys Ala Glu Glu
    50                  55                  60

Val Glu Arg Lys Gln Asn Arg Ile Tyr Tyr Ser Lys Pro Arg Ser Glu
65                  70                  75                  80

Met Gly Val Thr Cys Val Gly Arg Gln Lys Ile Lys Leu Gly Ser Lys
                85                  90                  95

Pro Leu Ile


<210> SEQ ID NO 13
<211> LENGTH: 21
<212> TYPE: PRT
<213> ORGANISM: Enterobacteria phage lambda

<400> SEQUENCE: 13

Asp Ala Gln Thr Arg Arg Arg Glu Arg Arg Ala Glu Lys Gln Ala Gln
1               5                   10                  15

Trp Lys Ala Ala Asn
            20


<210> SEQ ID NO 14
<211> LENGTH: 25
<212> TYPE: PRT
<213> ORGANISM: Enterobacteria phage P22

<400> SEQUENCE: 14

Lys Ser Thr Phe Ala Gly Asn Ala Lys Thr Arg Arg His Glu Arg Arg
1               5                   10                  15

Arg Lys Leu Ala Ile Glu Arg Asp Thr
            20                  25


<210> SEQ ID NO 15
<211> LENGTH: 22
<212> TYPE: PRT
<213> ORGANISM: Enterobacteria phage Phi21

<400> SEQUENCE: 15

Glu Ser Lys Gly Thr Ala Lys Ser Arg Tyr Lys Ala Arg Arg Ala Glu
1               5                   10                  15

Leu Ile Ala Glu Arg Arg
            20
```

<210> SEQ ID NO 16
<211> LENGTH: 15
<212> TYPE: RNA
<213> ORGANISM: Enterobacteria phage lambda

<400> SEQUENCE: 16
gcccugaaga agggc 15

<210> SEQ ID NO 17
<211> LENGTH: 15
<212> TYPE: RNA
<213> ORGANISM: Enterobacteria phage lambda

<400> SEQUENCE: 17
gcccugaaaa agggc 15

<210> SEQ ID NO 18
<211> LENGTH: 15
<212> TYPE: RNA
<213> ORGANISM: Enterobacteria phage P22

<400> SEQUENCE: 18
gcgcugacaa agcgc 15

<210> SEQ ID NO 19
<211> LENGTH: 20
<212> TYPE: RNA
<213> ORGANISM: Enterobacteria phage Phi21

<400> SEQUENCE: 19
uucaccucua accgggugag 20

<210> SEQ ID NO 20
<211> LENGTH: 410
<212> TYPE: PRT
<213> ORGANISM: Homo sapiens

<400> SEQUENCE: 20

Met Val Cys Phe Arg Leu Phe Pro Val Pro Gly Ser Gly Leu Val Leu
1 5 10 15

Val Cys Leu Val Leu Gly Ala Val Arg Ser Tyr Ala Leu Glu Leu Asn
20 25 30

Leu Thr Asp Ser Glu Asn Ala Thr Cys Leu Tyr Ala Lys Trp Gln Met
35 40 45

Asn Phe Thr Val Arg Tyr Glu Thr Thr Asn Lys Thr Tyr Lys Thr Val
50 55 60

Thr Ile Ser Asp His Gly Thr Val Thr Tyr Asn Gly Ser Ile Cys Gly
65 70 75 80

Asp Asp Gln Asn Gly Pro Lys Ile Ala Val Gln Phe Gly Pro Gly Phe
85 90 95

Ser Trp Ile Ala Asn Phe Thr Lys Ala Ala Ser Thr Tyr Ser Ile Asp
100 105 110

Ser Val Ser Phe Ser Tyr Asn Thr Gly Asp Asn Thr Thr Phe Pro Asp
115 120 125

Ala Glu Asp Lys Gly Ile Leu Thr Val Asp Glu Leu Leu Ala Ile Arg
130 135 140

Ile Pro Leu Asn Asp Leu Phe Arg Cys Asn Ser Leu Ser Thr Leu Glu
145 150 155 160

```
Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Asp Cys
        355                 360                 365

Ser Ala Asp Asp Asp Asn Phe Leu Val Pro Ile Ala Val Gly Ala Ala
    370                 375                 380

Leu Ala Gly Val Leu Ile Leu Val Leu Leu Ala Tyr Phe Ile Gly Leu
385                 390                 395                 400

Lys His His His Ala Gly Tyr Glu Gln Phe
                405                 410


<210> SEQ ID NO 21
<211> LENGTH: 410
<212> TYPE: PRT
<213> ORGANISM: Homo sapiens

<400> SEQUENCE: 21

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125
```

```
Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Glu Cys
        355                 360                 365

Ser Leu Asp Asp Asp Thr Ile Leu Ile Pro Ile Ile Val Gly Ala Gly
    370                 375                 380

Leu Ser Gly Leu Ile Ile Val Ile Val Ile Ala Tyr Val Ile Gly Arg
385                 390                 395                 400

Arg Lys Ser Tyr Ala Gly Tyr Gln Thr Leu
                405                 410


<210> SEQ ID NO 22
<211> LENGTH: 411
<212> TYPE: PRT
<213> ORGANISM: Homo sapiens

<400> SEQUENCE: 22

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
```

```
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Glu Glu Cys
        355                 360                 365

Ser Ala Asp Ser Asp Leu Asn Phe Leu Ile Pro Val Ala Val Gly Val
    370                 375                 380

Ala Leu Gly Phe Leu Ile Ile Val Val Phe Ile Ser Tyr Met Ile Gly
385                 390                 395                 400

Arg Arg Lys Ser Arg Thr Gly Tyr Gln Ser Val
                405                 410


<210> SEQ ID NO 23
<211> LENGTH: 10
<212> TYPE: PRT
<213> ORGANISM: Homo sapiens

<400> SEQUENCE: 23

Lys His His His Ala Gly Tyr Glu Gln Phe
1               5                   10


<210> SEQ ID NO 24
<211> LENGTH: 11
<212> TYPE: PRT
<213> ORGANISM: Homo sapiens
```

<400> SEQUENCE: 24

Arg Arg Lys Ser Tyr Ala Gly Tyr Gln Thr Leu
1 5 10

<210> SEQ ID NO 25
<211> LENGTH: 11
<212> TYPE: PRT
<213> ORGANISM: Homo sapiens

<400> SEQUENCE: 25

Arg Arg Lys Ser Arg Thr Gly Tyr Gln Ser Val
1 5 10

<210> SEQ ID NO 26
<211> LENGTH: 417
<212> TYPE: PRT
<213> ORGANISM: Homo sapiens

<400> SEQUENCE: 26

Met Ala Ala Pro Gly Ser Ala Arg Arg Pro Leu Leu Leu Leu Leu Leu
1 5 10 15

Leu Leu Leu Leu Gly Leu Met His Cys Ala Ser Ala Ala Met Phe Met
20 25 30

Val Lys Asn Gly Asn Gly Thr Ala Cys Ile Met Ala Asn Phe Ser Ala
35 40 45

Ala Phe Ser Val Asn Tyr Asp Thr Lys Ser Gly Pro Lys Asn Met Thr
50 55 60

Phe Asp Leu Pro Ser Asp Ala Thr Val Val Leu Asn Arg Ser Ser Cys
65 70 75 80

Gly Lys Glu Asn Thr Ser Asp Pro Ser Leu Val Ile Ala Phe Gly Arg
85 90 95

Gly His Thr Leu Thr Leu Asn Phe Thr Arg Asn Ala Thr Arg Tyr Ser
100 105 110

Val Gln Leu Met Ser Phe Val Tyr Asn Leu Ser Asp Thr His Leu Phe
115 120 125

Pro Asn Ala Ser Ser Lys Glu Ile Lys Thr Val Glu Ser Ile Thr Asp
130 135 140

Ile Arg Ala Asp Ile Asp Lys Lys Tyr Arg Cys Val Ser Gly Thr Gln
145 150 155 160

Val His Met Asn Asn Val Thr Val Thr Leu His Asp Ala Thr Ile Gln
165 170 175

Ala Tyr Leu Ser Asn Ser Ser Phe Ser Arg Gly Glu Thr Arg Cys Glu
180 185 190

Gln Asp Arg Pro Ser Pro Thr Thr Ala Pro Pro Ala Pro Pro Ser Pro
195 200 205

Ser Pro Ser Pro Val Pro Lys Ser Pro Ser Val Asp Lys Tyr Asn Val
210 215 220

Ser Gly Thr Asn Gly Thr Cys Leu Leu Ala Ser Met Gly Leu Gln Leu
225 230 235 240

Asn Leu Thr Tyr Glu Arg Lys Asp Asn Thr Thr Val Thr Arg Leu Leu
245 250 255

Asn Ile Asn Pro Asn Lys Thr Ser Ala Ser Gly Ser Cys Gly Ala His
260 265 270

Leu Val Thr Leu Glu Leu His Ser Glu Gly Thr Thr Val Leu Leu Phe
275 280 285

Gln Phe Gly Met Asn Ala Ser Ser Ser Arg Phe Phe Leu Gln Gly Ile

```
    290                 295                 300

Gln Leu Asn Thr Ile Leu Pro Asp Ala Arg Asp Pro Ala Phe Lys Ala
305                 310                 315                 320

Ala Asn Gly Ser Leu Arg Ala Leu Gln Ala Thr Val Gly Asn Ser Tyr
                325                 330                 335

Lys Cys Asn Ala Glu Glu His Val Arg Val Thr Lys Ala Phe Ser Val
            340                 345                 350

Asn Ile Phe Lys Val Trp Val Gln Ala Phe Lys Val Glu Gly Gly Gln
        355                 360                 365

Phe Gly Ser Val Glu Glu Cys Leu Leu Asp Glu Asn Ser Met Leu Ile
    370                 375                 380

Pro Ile Ala Val Gly Gly Ala Leu Ala Gly Leu Val Leu Ile Val Leu
385                 390                 395                 400

Ile Ala Tyr Leu Val Gly Arg Lys Arg Ser His Ala Gly Tyr Gln Thr
                405                 410                 415

Ile


<210> SEQ ID NO 27
<211> LENGTH: 11
<212> TYPE: PRT
<213> ORGANISM: Homo sapiens

<400> SEQUENCE: 27

Arg Lys Arg Ser His Ala Gly Tyr Gln Thr Ile
1               5                   10


<210> SEQ ID NO 28
<211> LENGTH: 238
<212> TYPE: PRT
<213> ORGANISM: Homo sapiens

<400> SEQUENCE: 28

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
    130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Ile Asn Val Thr Val Gly
                165                 170                 175

Cys Gly Ile Asn Phe Asn Glu Lys Ala Ile His Lys Glu Gly Cys Val
            180                 185                 190
```

```
Glu Lys Ile Gly Gly Trp Leu Arg Lys Asn Val Leu Val Val Ala Ala
        195                 200                 205

Ala Ala Leu Gly Ile Ala Phe Val Glu Val Leu Gly Ile Val Phe Ala
    210                 215                 220

Cys Cys Leu Val Lys Ser Ile Arg Ser Gly Tyr Glu Val Met
225                 230                 235


<210> SEQ ID NO 29
<211> LENGTH: 215
<212> TYPE: PRT
<213> ORGANISM: Homo sapiens

<400> SEQUENCE: 29

Met Ala Val Glu Gly Gly Met Lys Cys Val Lys Phe Leu Leu Tyr Val
1               5                   10                  15

Leu Leu Leu Ala Phe Cys Gly Ala Thr Pro Gly Ser Leu Leu Pro Val
            20                  25                  30

Val Ile Ile Ala Val Gly Val Phe Leu Phe Leu Val Ala Phe Val Gly
        35                  40                  45

Cys Cys Gly Ala Cys Lys Glu Asn Tyr Cys Leu Met Ile Thr Phe Ala
    50                  55                  60

Ile Phe Leu Ser Leu Ile Met Leu Val Glu Val Ala Ala Ala Ile Ala
65                  70                  75                  80

Gly Tyr Val Phe Arg Asp Lys Val Met Ser Glu Phe Asn Asn Asn Phe
                85                  90                  95

Arg Gln Gln Met Glu Asn Tyr Pro Lys Asn Asn His Thr Ala Ser Ile
            100                 105                 110

Leu Asp Arg Met Gln Ala Asp Phe Lys Cys Cys Gly Ala Ala Asn Tyr
        115                 120                 125

Thr Asp Trp Glu Lys Ile Pro Ser Met Ser Lys Asn Arg Val Pro Asp
    130                 135                 140

Ser Cys Cys Ile Asn Val Thr Val Gly Cys Gly Ile Asn Phe Asn Glu
145                 150                 155                 160

Lys Ala Ile His Lys Glu Gly Cys Val Glu Lys Ile Gly Gly Trp Leu
                165                 170                 175

Arg Lys Asn Val Leu Val Val Ala Ala Ala Ala Leu Gly Ile Ala Phe
            180                 185                 190

Val Glu Val Leu Gly Ile Val Phe Ala Cys Cys Leu Val Lys Ser Ile
        195                 200                 205

Arg Ser Gly Tyr Glu Val Met
    210                 215


<210> SEQ ID NO 30
<211> LENGTH: 166
<212> TYPE: PRT
<213> ORGANISM: Homo sapiens

<400> SEQUENCE: 30

Cys Gly Ala Cys Lys Glu Asn Tyr Cys Leu Met Ile Thr Phe Ala Ile
1               5                   10                  15

Phe Leu Ser Leu Ile Met Leu Val Glu Val Ala Ala Ala Ile Ala Gly
            20                  25                  30

Tyr Val Phe Arg Asp Lys Val Met Ser Glu Phe Asn Asn Asn Phe Arg
        35                  40                  45

Gln Gln Met Glu Asn Tyr Pro Lys Asn Asn His Thr Ala Ser Ile Leu
    50                  55                  60
```

```
Asp Arg Met Gln Ala Asp Phe Lys Cys Cys Gly Ala Ala Asn Tyr Thr
65                  70                  75                  80

Asp Trp Glu Lys Ile Pro Ser Met Ser Lys Asn Arg Val Pro Asp Ser
                85                  90                  95

Cys Cys Ile Asn Val Thr Val Gly Cys Gly Ile Asn Phe Asn Glu Lys
            100                 105                 110

Ala Ile His Lys Glu Gly Cys Val Glu Lys Ile Gly Gly Trp Leu Arg
        115                 120                 125

Lys Asn Val Leu Val Val Ala Ala Ala Ala Leu Gly Ile Ala Phe Val
    130                 135                 140

Glu Val Leu Gly Ile Val Phe Ala Cys Cys Leu Val Lys Ser Ile Arg
145                 150                 155                 160

Ser Gly Tyr Glu Val Met
                165


<210> SEQ ID NO 31
<211> LENGTH: 14
<212> TYPE: PRT
<213> ORGANISM: Homo sapiens

<400> SEQUENCE: 31

Cys Cys Leu Val Lys Ser Ile Arg Ser Gly Tyr Glu Val Met
1               5                   10


<210> SEQ ID NO 32
<211> LENGTH: 478
<212> TYPE: PRT
<213> ORGANISM: Homo sapiens

<400> SEQUENCE: 32

Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Pro Leu Pro Val Tyr Thr Gln Phe
    50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Glu Leu Arg Asn
                85                  90                  95

Lys Ala Asn Ile Gln Phe Gly Asp Asn Gly Thr Thr Ile Ser Ala Val
            100                 105                 110

Ser Asn Lys Ala Tyr Val Phe Glu Arg Asp Gln Ser Val Gly Asp Pro
        115                 120                 125

Lys Ile Asp Leu Ile Arg Thr Leu Asn Ile Pro Val Leu Thr Val Ile
    130                 135                 140

Glu Trp Ser Gln Val His Phe Leu Arg Glu Ile Ile Glu Ala Met Leu
145                 150                 155                 160

Lys Ala Tyr Gln Gln Lys Leu Phe Val Thr His Thr Val Asp Glu Leu
                165                 170                 175

Leu Trp Gly Tyr Lys Asp Glu Ile Leu Ser Leu Ile His Val Phe Arg
            180                 185                 190

Pro Asp Ile Ser Pro Tyr Phe Gly Leu Phe Tyr Glu Lys Asn Gly Thr
        195                 200                 205
```

```
Asn Asp Gly Asp Tyr Val Phe Leu Thr Gly Glu Asp Ser Tyr Leu Asn
    210                 215                 220

Phe Thr Lys Ile Val Glu Trp Asn Gly Lys Thr Ser Leu Asp Trp Trp
225                 230                 235                 240

Ile Thr Asp Lys Cys Asn Met Ile Asn Gly Thr Asp Gly Asp Ser Phe
                245                 250                 255

His Pro Leu Ile Thr Lys Asp Glu Val Leu Tyr Val Phe Pro Ser Asp
            260                 265                 270

Phe Cys Arg Ser Val Tyr Ile Thr Phe Ser Asp Tyr Glu Ser Val Gln
        275                 280                 285

Gly Leu Pro Ala Phe Arg Tyr Lys Val Pro Ala Glu Ile Leu Ala Asn
    290                 295                 300

Thr Ser Asp Asn Ala Gly Phe Cys Ile Pro Glu Gly Asn Cys Leu Gly
305                 310                 315                 320

Ser Gly Val Leu Asn Val Ser Ile Cys Lys Asn Gly Ala Pro Ile Ile
                325                 330                 335

Met Ser Phe Pro His Phe Tyr Gln Ala Asp Glu Arg Phe Val Ser Ala
            340                 345                 350

Ile Glu Gly Met His Pro Asn Gln Glu Asp His Glu Thr Phe Val Asp
        355                 360                 365

Ile Asn Pro Leu Thr Gly Ile Ile Leu Lys Ala Ala Lys Arg Phe Gln
    370                 375                 380

Ile Asn Ile Tyr Val Lys Lys Leu Asp Asp Phe Val Glu Thr Gly Asp
385                 390                 395                 400

Ile Arg Thr Met Val Phe Pro Val Met Tyr Leu Asn Glu Ser Val His
                405                 410                 415

Ile Asp Lys Glu Thr Ala Ser Arg Leu Lys Ser Met Ile Asn Thr Thr
            420                 425                 430

Leu Ile Ile Thr Asn Ile Pro Tyr Ile Ile Met Ala Leu Gly Val Phe
        435                 440                 445

Phe Gly Leu Val Phe Thr Trp Leu Ala Cys Lys Gly Gln Gly Ser Met
    450                 455                 460

Asp Glu Gly Thr Ala Asp Glu Arg Ala Pro Leu Ile Arg Thr
465                 470                 475


<210> SEQ ID NO 33
<211> LENGTH: 335
<212> TYPE: PRT
<213> ORGANISM: Homo sapiens

<400> SEQUENCE: 33

Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Pro Leu Pro Val Tyr Thr Gln Phe
    50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Ser Leu Asp Trp
                85                  90                  95

Trp Ile Thr Asp Lys Cys Asn Met Ile Asn Gly Thr Asp Gly Asp Ser
```

```
            100                 105                 110

Phe His Pro Leu Ile Thr Lys Asp Glu Val Leu Tyr Val Phe Pro Ser
        115                 120                 125

Asp Phe Cys Arg Ser Val Tyr Ile Thr Phe Ser Asp Tyr Glu Ser Val
    130                 135                 140

Gln Gly Leu Pro Ala Phe Arg Tyr Lys Val Pro Ala Glu Ile Leu Ala
145                 150                 155                 160

Asn Thr Ser Asp Asn Ala Gly Phe Cys Ile Pro Glu Gly Asn Cys Leu
                165                 170                 175

Gly Ser Gly Val Leu Asn Val Ser Ile Cys Lys Asn Gly Ala Pro Ile
            180                 185                 190

Ile Met Ser Phe Pro His Phe Tyr Gln Ala Asp Glu Arg Phe Val Ser
        195                 200                 205

Ala Ile Glu Gly Met His Pro Asn Gln Glu Asp His Glu Thr Phe Val
    210                 215                 220

Asp Ile Asn Pro Leu Thr Gly Ile Ile Leu Lys Ala Ala Lys Arg Phe
225                 230                 235                 240

Gln Ile Asn Ile Tyr Val Lys Lys Leu Asp Asp Phe Val Glu Thr Gly
                245                 250                 255

Asp Ile Arg Thr Met Val Phe Pro Val Met Tyr Leu Asn Glu Ser Val
            260                 265                 270

His Ile Asp Lys Glu Thr Ala Ser Arg Leu Lys Ser Met Ile Asn Thr
        275                 280                 285

Thr Leu Ile Ile Thr Asn Ile Pro Tyr Ile Ile Met Ala Leu Gly Val
    290                 295                 300

Phe Phe Gly Leu Val Phe Thr Trp Leu Ala Cys Lys Gly Gln Gly Ser
305                 310                 315                 320

Met Asp Glu Gly Thr Ala Asp Glu Arg Ala Pro Leu Ile Arg Thr
                325                 330                 335


<210> SEQ ID NO 34
<211> LENGTH: 19
<212> TYPE: PRT
<213> ORGANISM: Homo sapiens

<400> SEQUENCE: 34

Gly Gln Gly Ser Met Asp Glu Gly Thr Ala Asp Glu Arg Ala Pro Leu
1               5                   10                  15

Ile Arg Thr
```